United States Patent
May, Jr.

(10) Patent No.: US 11,338,105 B2
(45) Date of Patent: May 24, 2022

(54) RESPIRATORY HUMIDIFICATION DEVICE

(71) Applicant: Frederick A May, Jr., The Ponds (AU)

(72) Inventor: Frederick A May, Jr., The Ponds (AU)

(73) Assignee: GLOBALMED, INC., Trenton (CA)

( * ) Notice: Subject to any disclaimer, the term of this patent is extended or adjusted under 35 U.S.C. 154(b) by 359 days.

(21) Appl. No.: 16/362,686

(22) Filed: Mar. 24, 2019

(65) Prior Publication Data

US 2019/0298962 A1    Oct. 3, 2019

Related U.S. Application Data

(60) Provisional application No. 62/648,812, filed on Mar. 27, 2018.

(51) Int. Cl.
     *A61M 16/10*      (2006.01)
     *A61M 16/00*      (2006.01)

(52) U.S. Cl.
     CPC .... *A61M 16/1095* (2014.02); *A61M 16/0003* (2014.02); *A61M 16/109* (2014.02); *A61M 16/1045* (2013.01); *A61M 2016/0033* (2013.01); *A61M 2205/3368* (2013.01); *A61M 2205/502* (2013.01)

(58) Field of Classification Search
     CPC .............. A61M 16/00; A61M 16/1045; A61M 16/1075; A61M 16/109; A61M 16/16; A61M 16/162; A61M 16/164; A61M 16/165; A61M 16/167; A61M 16/168
     See application file for complete search history.

(56) References Cited

U.S. PATENT DOCUMENTS

| | | | |
|---|---|---|---|
| 1,995,302 A | 3/1935 | Goldstein | 128/254 |
| 3,912,795 A | 10/1975 | Jackson | A61M 15/00 |
| | | | 261/36 |
| 4,010,748 A | 3/1977 | Dobritz | A61M 16/00 |
| | | | 128/192 |

(Continued)

FOREIGN PATENT DOCUMENTS

| | | | |
|---|---|---|---|
| EP | 0950424 B1 | 3/1999 | ............ A61M 25/00 |
| EP | 2119466 A1 * | 11/2009 | .......... A61M 16/167 |
| FR | 2303663 | 3/1975 | |

*Primary Examiner* — Joseph D. Boecker
(74) *Attorney, Agent, or Firm* — David A. Burge; Benjamin D. Burge

(57) ABSTRACT

A respiratory humidification device includes: a casing; a separator wall to divide an interior space into filling and humidification chambers, wherein a bottom edge of the separator wall leaves a space between it and the casing bottom to define a passage allowing water to flow atop the casing bottom between the chambers, and enabling the water level to rise enough to block the passage to prevent respiratory gas from passing therethrough; a valve and float within the filling chamber to control water flow into the filling chamber to prevent the water level from rising higher than a threshold; and wherein an outer wall of the casing and the separator wall cooperate with the water surface within the humidification chamber to define an elongate tube-like pathway through which respiratory gas proceeds along a path extending generally parallel to the water surface within the humidification chamber to be humidified.

17 Claims, 28 Drawing Sheets

(56) References Cited

U.S. PATENT DOCUMENTS

| | | | |
|---|---|---|---|
| 4,048,993 A | 9/1977 | Dobritz | A61M 16/00 128/212 |
| 4,051,205 A * | 9/1977 | Grant | A61M 16/1075 261/70 |
| 4,543,951 A | 10/1985 | Phue | A61M 16/00 128/204.25 |
| 4,621,632 A | 11/1986 | Bartels et al. | A61M 16/00 128/203.27 |
| 4,686,354 A | 8/1987 | Makin | A61M 16/15 219/301 |
| 4,708,831 A | 11/1987 | Elsworth et al. | A61M 16/16 261/130 |
| 4,722,334 A | 2/1988 | Blackmer et al. | A61M 16/00 128/203.16 |
| 4,773,410 A | 9/1988 | Blackmer et al. | A61M 16/00 128/203.26 |
| 4,829,998 A | 5/1989 | Jackson | A61M 15/00 128/203.12 |
| 4,941,469 A | 7/1990 | Adahan | A61M 16/16 128/205.18 |
| 5,031,612 A | 7/1991 | Clementi | A61M 16/16 128/204.14 |
| 5,101,820 A | 4/1992 | Christopher | A61M 16/00 128/204.18 |
| 5,357,948 A | 10/1994 | Eilentropp | A61M 15/00 128/204.17 |
| 5,392,770 A | 2/1995 | Clawson et al. | A61M 16/00 128/203.77 |
| 5,537,996 A | 7/1996 | McPhee | A61M 16/16 128/204.17 |
| 5,640,951 A | 6/1997 | Huddart et al. | A61M 16/00 128/204.77 |
| 5,988,164 A | 11/1999 | Paluch | A61M 16/00 128/203.26 |
| 6,050,260 A | 4/2000 | Daniell et al. | A61M 16/00 128/204.22 |
| 6,125,847 A | 10/2000 | Lin | A61M 16/00 128/204.17 |
| 6,272,933 B1 | 8/2001 | Gradon et al. | G01F 1/00 73/861 |
| 6,349,722 B1 | 2/2002 | Gradon et al. | A61M 15/00 128/203.17 |
| 6,363,930 B1 | 4/2002 | Clawson et al. | A62B 18/08 128/201.13 |
| 6,394,084 B1 | 5/2002 | Nitta | A62B 18/08 128/201.13 |
| 6,554,260 B1 | 4/2003 | Lipscombe et al. | B01F 3/04 261/142 |
| 6,584,972 B2 | 7/2003 | McPhee | A61M 15/00 128/203.17 |
| 6,659,136 B2 | 12/2003 | Fukui et al. | F16L 11/00 138/125 |
| 6,694,974 B1 | 2/2004 | GeorgeGradon et al. | A61M 15/00 128/203.17 |
| 6,718,973 B2 | 4/2004 | Koch | A61M 15/00 128/203.16 |
| 6,918,389 B2 | 7/2005 | Seakins et al. | H05B 3/00 128/203.27 |
| 6,935,337 B2 | 8/2005 | Virr et al. | A61M 15/00 128/203.16 |
| 7,096,864 B1 | 8/2006 | Mayer et al. | A62B 9/04 128/202.27 |
| 7,137,388 B2 | 11/2006 | Virr et al. | A61M 11/00 128/203.17 |
| 7,478,635 B2 | 1/2009 | Wixey et al. | A61M 11/00 128/203.17 |
| 7,588,029 B2 | 9/2009 | Smith et al. | A61M 15/00 128/203.17 |
| 7,962,018 B2 | 6/2011 | Hunt et al. | F24F 6/00 392/394 |
| 8,006,691 B2 | 8/2011 | Kenyon et al. | A62B 9/00 128/200.24 |
| 8,015,971 B2 | 9/2011 | Kwok | A61M 16/00 128/204.17 |
| 8,063,343 B2 | 11/2011 | McGhin et al. | H05B 1/02 219/497 |
| 8,078,040 B2 | 12/2011 | Forrester | F24H 1/10 392/481 |
| 8,186,345 B2 | 4/2012 | Payton et al. | A61M 11/00 128/204.17 |
| 8,333,195 B2 | 12/2012 | Cortez, Jr. et al. | F23D 11/00 128/203.26 |
| 8,360,059 B2 | 1/2013 | Koulechov et al. | A61M 16/00 123/204.17 |
| 8,453,641 B2 | 6/2013 | Payton et al. | A61M 11/00 128/204.17 |
| 8,453,681 B2 | 6/2013 | Forrester et al. | F16L 11/118 138/122 |
| 8,550,075 B2 | 10/2013 | Virr | A61M 16/16 128/203.27 |
| 8,631,789 B2 | 1/2014 | Virr et al. | A61M 15/00 128/204.18 |
| 8,739,780 B2 | 6/2014 | Tang et al. | A61M 11/00 128/203.14 |
| 8,833,367 B2 | 9/2014 | Kwok | A61M 16/10 128/204.22 |
| 8,893,715 B2 | 11/2014 | Payton et al. | F23D 14/00 128/204.18 |
| 9,186,477 B2 | 11/2015 | Hunt et al. | F24F 6/00 128/203 |
| 9,505,164 B2 | 11/2016 | Garrett et al. | B29C 53/582 156/244.11 |
| 9,707,370 B2 | 7/2017 | Smith et al. | A61M 11/00 128/203.26 |
| 9,717,874 B2 | 8/2017 | Smith et al. | A61M 16/0875 428/139 |
| RE46,543 E | 9/2017 | Trevor-Wilson et al. | A61M 16/00 |
| D798,428 S | 9/2017 | Cork et al. | B01D 46/02 D23/360 |
| 9,750,916 B2 | 9/2017 | Magee | A61M 16/10 261/142 |
| RE46,571 E | 10/2017 | Virr et al. | A61M 16/16 |
| 9,821,135 B2 | 11/2017 | Tang et al. | A61M 16/16 128/202.22 |
| 10,252,017 B2 | 4/2019 | Smith et al. | A61M 16/08 |
| 10,272,221 B2 | 4/2019 | Foote | F24F 6/02 |
| 10,279,141 B2 | 5/2019 | Virr et al. | A61M 16/00 |
| 10,293,121 B2 | 5/2019 | Blackhurst et al. | A61B 1/00 |
| 10,307,560 B2 | 6/2019 | Martin et al. | A61M 16/16 |
| 2010/0242963 A1* | 9/2010 | Brieger | A61M 16/167 128/203.26 |
| 2011/0156289 A1* | 6/2011 | Steg | A61M 16/16 261/70 |
| 2013/0306075 A1 | 11/2013 | Payton et al. | A61M 16/00 128/205.23 |
| 2014/0158125 A1 | 6/2014 | O'Donnell et al. | A61L 2/24 128/203.14 |
| 2015/0020801 A1 | 1/2015 | Frame et al. | A61M 16/00 128/202.22 |
| 2015/0108670 A1 | 4/2015 | Magee | A61M 16/1045 |
| 2015/0165157 A1 | 6/2015 | Payton et al. | A61M 16/16 |
| 2015/0202402 A1 | 7/2015 | Kat | A61M 16/16 |
| 2015/0217079 A1 | 8/2015 | Meauley et al. | A61M 16/10 |
| 2016/0101257 A1 | 4/2016 | Lee et al. | A61M 16/1095 |
| 2016/0193437 A1 | 7/2016 | Bao et al. | A61M 16/00 |
| 2017/0000968 A1 | 1/2017 | Harrington | A61M 16/16 |
| 2017/0182280 A1 | 6/2017 | Leonard | A61M 16/145 |
| 2018/0214657 A1 | 8/2018 | Forrester | A61M 16/1045 |
| 2018/0214658 A1 | 8/2018 | Forrester | A61M 16/1045 |
| 2018/0214659 A1 | 8/2018 | Forrester | A61M 16/1095 |

\* cited by examiner

RESPIRATORY HUMIDIFICATION DEVICE

REFERENCE TO PROVISIONAL APPLICATION

This Utility patent application claims the benefit of the filing date of Provisional Application Ser. No. 62/648,812 filed Mar. 27, 2018 by Frederick A. May, Jr., and entitled RESPIRATORY HUMIDIFICATION DEVICE, the disclosure of which is incorporated herein by reference in its entirety.

BACKGROUND

The present invention relates to the field of respiratory humidification devices to add heat and/or water vapor to respiratory gases provided to patients as part of treating various medical conditions, such as traumatic lung injury, sleep apnea, asthma, chronic obstructive pulmonary disease (COPD), hypoxemia and hypotension. Such a respiratory humidification device may be used in conjunction with, or may otherwise be incorporated into, a medical device, such as a ventilator or continuous positive airway pressure (CPAP) device. Alternatively or additionally, such a respiratory humidification device may be used in conjunction with, or may otherwise be incorporated into, a hose assembly that conveys respiratory gases between such a medical device and a face mask, an endotracheal tube or tracheostomy stoma of a patient. Such equipment may be used in a hospital or other medical facility, or may be used at a patient's home, such as at a patient's bedside while sleeping.

It is usually deemed desirable for such gases conveyed to a patient to include some degree of water vapor to avoid drying tissues of a patient's respiratory system. Especially in a situation in which a ventilator, CPAP device or other medical device is to be used to provide respiratory gases to a patient for an extended period of time, it is usually deemed desirable for such gases to include some amount of water vapor to avoid drying tissues of a patient's respiratory system. As will be familiar to medical personnel, the provision of insufficiently moistened respiratory gases can cause inflammation and/or other conditions in the throat, trachea, bronchi and/or air sacks within the lungs, thereby potentially damaging such tissues to an extent that may lead to any of a variety of harmful conditions.

It is also usually deemed desirable for such gases to be heated to a controlled degree to better enable a patient to maintain a healthy core body temperature and/or increase the capacity of the respiratory gases to absorb water. As will be familiar to those skilled in the art, the ability of air and other mixtures of breathable gas to absorb water vapor is partially determined by temperature, with warmer gases being able to absorb more water vapor, thereby enabling sufficient absorption of water vapor to be achieved.

Achieving sufficient absorption of water vapor into respiratory gases conveyed to patients has proven to be an issue with prior art respiratory humidification devices. As will be familiar to those skilled in the art, lung capacities, rates of breathing, and/or other respiratory system characteristics vary greatly from patient to patient, especially when the wide variety of breathing-related ailments that each patient may have is also taken into account. As a result, ventilators, CPAP devices and/or other medical devices that provide respiratory gases are caused to do so at breathing rates and/or volumes per breath that are adjustable. However, prior art respiratory humidification devices have been found to be incapable of providing a consistent degree of humidification across a sufficient range of such adjustments. As a result, relatively minor adjustments to the manner in which a ventilator, CPAP device or other medical device provides respiratory gases to a patient may beget wildly varying and unpredictable changes in the degree of humidification provided.

Achieving consistent heating of respiratory gases conveyed to patients to enable sufficient absorption of water vapor and/or to prevent condensation within the hose assembly that extends between prior art respiratory humidification devices and patients has also proven to be an issue. Additionally, and as will be familiar to those skilled in the art, the respiratory gases that a patient breathes out also typically include some amount of water vapor. If the temperature of the gases in one of the hoses that conveys gases to a patient or from a patient falls below the dew point of the gases within that hose, then water vapor condenses within that hose, and possibly leads to pooling of liquid water within the lowest portion of the hose. As a result, the flow of gases through that hose may be constricted or even cut off entirely in a manner very much akin to the pooling of water within a sink drain trap. Depending on where such pooling occurs within a hose, and depending on which hose such pooling occurs within, it is possible for a patient to be caused to breathe in pooled water and/or for pooled water to be sent into the medical device that provides a patient with respiratory gases. Such developments may be acutely and immediately harmful to the patient such that the patient may be caused to actually drown from inhalation of liquid water into the lungs, and/or the medical device may be damaged by the intake of liquid water, instead of gases breathed out by the patient.

It is commonplace for a ventilator, CPAP device and/or other medical devices to incorporate a heating component (e.g., an electrically powered hot plate) atop which a respiratory humidification device is placed to be heated as part of effecting humidification of respiratory gases. The amount of heat that is provided by the medical device is usually automatically varied in response to the temperature and/or flow rate of respiratory gases conveyed between the medical device and the patient as detected by sensors. However, just as previously described with regard to varying flow rate and/or volume of gases per breath, many prior art respiratory humidification devices have been found to also provide unpredictable degrees of humidification when the amount of heat that is provided is varied.

FIG. 1 depicts a typical PRIOR ART respiratory humidification device 200 that embodies various prior art efforts at adding water vapor to respiratory gases that are conveyed to patients. As depicted, such a prior art device 200 is often designed in a manner that resembles an enclosed kettle or cooking pot that provides a relatively large open interior through which respiratory gases are caused to flow. An amount of water 988 is retained at the bottom of the open volume, and is continuously replenished with the assistance of gravity from an external water source 980. The prior art device 200 is often placed atop a heating component 991 to be heated.

As can be seen, such typical prior art humidifying devices are not designed to in any way control any aspect of the flow of respiratory gases through the portion of the open volume that is above the surface of the water retained therein. As a result, the respiratory gases are allowed to follow any of a wide variety of paths 209 therethrough. Thus, only a portion of the flow of respiratory gases passing therethrough does come into contact with the surface of the water 988 to thereby be humidified. Meanwhile, another significant portion of the flow of respiratory gases passing therethrough never comes into such contact with the surface of the water 988, and therefore, may receive little or no humidification. As a result, the ability of such typical prior art respiratory humidification devices 200 to humidify respiratory gases is greatly limited.

Additionally, and as those skilled in the art will readily recognize, the introduction of a flow of a gas through such an open interior often causes the formation of a complex set of turbulent currents among the paths 209 of the gas within the open interior. Such a complex set of turbulent currents are not specifically depicted in FIG. 1 for sake of simplicity in depicting the aforementioned situation in which a significant portion of the flow of gases pass through such an open interior along paths 209 that result in no contact being made with the surface of the water retained therein. However, as those skilled in the art will readily recognize, the pattern and strengths of each of the currents in such a complex set of turbulent currents can change greatly and in unpredictable ways based on such factors as changes in the volume and/or rate of flow of gases through such an open interior, changes in the level of the water 988 within the open interior, and/or changes in the amount of heat introduced into the open interior.

Such great changes in such a complex set of currents can greatly change the relative portions of the flow of the gases that do and do not come into contact with the surface of the water 988, thereby changing the degree of humidification achieved. As a result, the effectiveness of such prior art respiratory humidification devices 200 can vary in unpredictable ways in response to even minor adjustments made for the needs of different patients and/or as a result of the even minor automatically implemented variations in the amount of heat applied to such prior art respiratory humidification devices. Stated more simply, the design of such prior art respiratory humidification devices allows too many variables to exert outsized and unpredictable effects on the degree of humidification.

SUMMARY

The present invention addresses such needs and deficiencies as are explained above by providing a respiratory humidification device that splits the flow of respiratory gases therethrough into a pair of semicircular paths that each bring the portion of respiratory gases that flow therealong into more thorough contact with the surface of the water contained therein. Along each of the two semicircular paths, the respiratory gases are caused to develop a spiraling flow that serves to enhance the thoroughness of the contact of the respiratory gases with the surface of the water, thereby ensuring more thorough heating of the respiratory gases and more thorough absorption of moisture by the respiratory gases before the respiratory gases are output to a hose assembly to be conveyed to a patient.

A respiratory humidification device may include: a casing that includes a casing top and a casing bottom that cooperate to enclose an interior space, wherein the casing bottom defines an underside portion of the casing that is formed from thermally conductive material to conduct heat into the interior space from a heating component positioned external to and underneath the casing to heat water within the casing; a separator wall within the interior space that extends downward from the casing top and toward the casing bottom to divide the interior space into a filling chamber and humidification chamber, wherein a bottom edge of the separator wall leaves a space between the separator wall and the casing bottom that defines a main passage between the filling chamber and the humidification chamber that allows the water to flow atop the casing bottom between the filling chamber and the humidification chamber, and that enables a level of the water within at least one of the filling chamber or the humidification chamber to rise high enough to block the main passage to prevent respiratory gas from passing therethrough; a valve and a first float within the filling chamber that cooperate to control a flow of the water into the filling chamber from a water source external to the casing to prevent the level of the water within at least the filling chamber from rising higher than a predetermined threshold level; a gas inlet formed through the casing top to enable entry of a main flow of the respiratory gas into the humidification chamber from a medical device external to the casing; a gas outlet formed through the casing top to enable the main flow of respiratory gas to proceed through the humidification chamber in a direction from the gas inlet to the gas outlet, and to be output from the gas outlet to a patient after humidification of the respiratory gas; and wherein at least one portion of an outer wall of the casing top and at least one portion of the separator wall are configured to cooperate with a surface of the water within the humidification chamber to define an elongate tube-like pathway between the gas inlet and the gas outlet through which at least one portion of the main flow of the respiratory gas is to proceed along a path that extends generally parallel to the surface of the water within the humidification chamber to enable humidification of the respiratory gas with the water within the humidification chamber.

The casing bottom may be shaped and sized to enable the respiratory humidification device to be supported by the casing bottom atop the heating component to place the casing bottom in thermally conductive contact with the heating component. The casing bottom may define at least a portion of both the filling chamber and the humidification chamber to enable heating of the water within both the filling chamber and the humidification chamber through the casing bottom by the heating component. The casing top may be formed from a thermally insulating material to increase retention, within the interior space, of the heat provided to the respiratory humidification device by the heating component. Another passage may be formed through the separator wall to enable another flow of the respiratory gas between the filling chamber and the humidification chamber that enables equalization of gas pressure between the filling chamber and the humidification chamber to enable the levels of the water within the filling chamber and the humidification chamber to be equalized at times when the level of the water within at least one of the filling chamber and the humidification chamber is high enough to block the main passage, wherein the other passage is smaller than the gas inlet, the gas outlet and the main passage, and wherein the other flow of the respiratory gas is smaller than the main flow of respiratory gas. At least a portion of the gas inlet and at least a portion of the gas outlet may be of an identical shape and size to enable the medical device to be connected to the gas outlet to cause the main flow of respiratory gas to proceed in an opposite direction through the humidification chamber from the gas outlet to the gas inlet, and to be output from the gas inlet to the patient; and the elongate tube-like pathway may be configured to enable the humidification of the respiratory gas to be as effective when the main flow proceeds in the opposite direction from the gas outlet to the gas inlet as in the direction from the gas inlet to the gas outlet.

The respiratory humidification device may further include a second float within the filling chamber to cooperate with the valve to control the flow of the water into the filling chamber from the water source to prevent the level of the water within at least the filling chamber from rising higher than the predetermined threshold level, wherein the cooperation between the valve and the first float to control the flow of the water into the filling chamber from the water source is independent of the cooperation between the valve and the second float to control the flow of the water into the filling chamber from the water source such that either of the cooperation between the valve and the first float or the cooperation between the valve and the second float is able to cause the flow of water in the filling chamber from the water source to be stopped to prevent the level of the water within at least the filling chamber from rising higher than the predetermined threshold level. The first float may be larger than and concentrically surround the second float.

The at least one the portion of the outer wall and the at least one portion of the separator wall may be configured to cooperate with the surface of the water within the humidification chamber to induce a horizontal vortex in the at least one portion of the main flow of the respiratory gas along the path to enhance the humidification of the respiratory gas within the humidification chamber. The respiratory humidification device may further include a heat spreader within the humidification chamber, wherein a lower portion of the heat spreader is positioned to extend downward into the water within the humidification chamber to absorb heat from the water within the humidification chamber, and an upper portion of the heat spreader is positioned to extend upward from the surface of the water within the humidification chamber and into the path of the at least one portion of the main flow of the respiratory gas to radiate the absorbed heat into the respiratory gas to enhance the humidification of the respiratory gas within the humidification chamber. The heat spreader may be configured to cooperate with the at least one the portion of the outer wall, the at least one portion of the separator wall or the surface of the water within the humidification chamber to induce a horizontal vortex in the at least one portion of the main flow of the respiratory gas along the path to enhance the humidification of the respiratory gas within the humidification chamber.

At least the portion of the outer wall may be formed to give at least a portion of the casing top a curve in its shape; and at least the portion of the outer wall and at least the portion of the separator wall may be configured to cooperate with the surface of the water within the humidification chamber to define the elongate tube-like pathway to be a semi-circular elongate tube-like pathway such that at least the portion of the main flow of the respiratory gas follows a semi-circular path between the gas inlet and the gas outlet. The outer wall may be formed to give at least a portion of the casing a cylindrical shape; the separator wall may be formed to define the humidification chamber as an annular humidification chamber that surrounds the filling chamber such that the filling chamber is nested concentrically within the annular humidification chamber; the outer wall and the separator wall may be configured to cooperate with the surface of the water within the annular humidification chamber to define a pair of semi-circular elongate tube-like pathways between the gas inlet and the gas outlet; the at least one portion of the of the main flow of the respiratory gas may proceed along the path that extends generally parallel to the surface of the water within the humidification chamber and through a first one of the pair of semi-circular elongate tube-like pathways; and at least one other portion of the main flow of the respiratory gas may proceed along another path that extends generally parallel to the surface of the water within the humidification chamber and through an second one of the pair of semi-circular elongate tube-like pathways.

The medical device may monitor at least one of a temperature and a rate of flow of the main flow of the respiratory gas from the respiratory humidification device to the patient; and the medical device adjusts an amount of the heat provided by the heating component to at least the casing bottom based on the at least one of the temperature and the rate of flow. The respiratory humidification device may further include the heating component. The respiratory humidification device may further include the medical device. The respiratory humidification device may further include an inspiratory hose assembly to convey the main flow of the respiratory gas from the humidification device after the humidification of the respiratory gas. The respiratory humidification device may further include an expiratory hose assembly to convey exhaled respiratory gas from the patient to the medical device.

A respiratory humidification device may include: a casing that includes a casing top having an at least partially cylindrical shape and a casing bottom having an at least partially circular shape that cooperate to enclose an interior space, wherein the casing bottom defines an underside portion of the casing that is formed from thermally conductive material to conduct heat into the interior space from a heating component positioned external to and underneath the casing to heat water within the casing; an at least partially cylindrical separator wall within the interior space that extends downward from the casing top and toward the casing bottom to divide the interior space into a filling chamber and an annular humidification chamber that surrounds the filling chamber, wherein a bottom edge of the separator wall leaves a space between the separator wall and the casing bottom that defines a main passage between the filling chamber and the humidification chamber that allows the water to flow atop the casing bottom between the filling chamber and the humidification chamber, and that enables a level of the water within at least one of the filling chamber or the humidification chamber to rise high enough to block the main opening to prevent respiratory gas from passing therethrough; a valve to control a flow of the water into the filling chamber from a water source external to the casing to prevent the level of the water within at least the filling chamber from rising higher than a predetermined threshold level; a gas inlet formed through the casing top to enable entry of a main flow of the respiratory gas into the humidification chamber from a medical device external to the casing; a gas outlet formed through the casing top at a location opposite from the gas inlet to enable the main flow of respiratory gas to proceed through the humidification chamber in a direction from the gas inlet to the gas outlet, and to be output from the gas outlet to a patient after humidification of the respiratory gas; and wherein at least the outer wall of the casing top and the separator wall are configured to cooperate with a surface of the water within the humidification chamber to define a pair of semi-circular elongate tube-like pathways around opposite sides of the filling chamber between the gas inlet and the gas outlet, the main flow of respiratory gas is divided into a pair of semi-circular flows of the respiratory gas that each proceed through a different one of the pair of semi-circular elongate tube-like pathways, and each semi-circular flow of the respiratory gas proceeds within its corresponding one of the pair of pathways along a corresponding one of a pair of semi-circular paths that extends generally parallel to the surface of the water within the humidification chamber to enable humidification of the respiratory gas with the water within the humidification chamber.

A method of humidifying a main flow of respiratory gas supplied by a medical device to a patient may include: conveying the main flow of the respiratory gas from the medical device to a gas inlet of a humidification chamber defined within an interior space of a casing of a humidification device; conveying the main flow of the respiratory gas from a gas outlet of the humidification chamber to the patient after humidification of the respiratory gas within the humidification chamber; providing a flow of water from a water source external to the casing to a water inlet of a filling chamber defined within the interior space of the casing; heating a casing bottom of the casing to heat the water within at least one of the filling chamber and the humidification chamber, wherein the casing bottom and a casing top of the casing cooperate to enclose the interior space, the casing bottom defines an underside portion of the casing that is formed from thermally conductive material to conduct heat into the interior space from a heating component positioned external to and underneath the casing to heat the water within the casing, a separator wall within the interior space extends downward from the casing top and toward the casing bottom to divide the interior space into the filling chamber and humidification chamber, and a bottom edge of the separator wall leaves a space between the separator wall and the casing bottom that defines a main passage between the filling chamber and the humidification chamber that allows the water to flow atop the casing bottom between the filling chamber and the humidification chamber, and that enables a level of the water within at least one of the filling chamber or the humidification chamber to rise high enough to block the main passage to prevent respiratory gas from passing therethrough; controlling the flow of water into the filling chamber from the water source to prevent the level of the water within at least the filling chamber from rising higher than a predetermine threshold level; and wherein at least one portion of an outer wall of the casing top and at least one portion of the separator wall are configured to cooperate with a surface of the water within the humidification chamber to define an elongate tube-like pathway between the gas inlet and the gas outlet through which at least one portion of the main flow of the respiratory gas is to proceed along a path that extends generally parallel to the surface of the water within the humidification chamber to enable humidification of the respiratory gas with the water within the humidification chamber.

A method of humidifying a main flow of respiratory gas supplied by a medical device to a patient may include: conveying the main flow of the respiratory gas from the medical device to a gas inlet of a humidification chamber defined within an interior space of a casing of a humidification device; conveying the main flow of the respiratory gas from a gas outlet of the humidification chamber to the patient after humidification of the respiratory gas within the humidification chamber; providing a flow of water from a water source external to the casing to a water inlet of a filling chamber defined within the interior space of the casing; heating a casing bottom of the casing to heat the water within at least one of the filling chamber and the humidification chamber, wherein the casing bottom and a casing top of the casing cooperate to enclose the interior space, the casing top has an at least partially cylindrical shape, the casing bottom has an at least partially circular shape, the casing bottom defines an underside portion of the casing that is formed from thermally conductive material to conduct heat into the interior space from a heating component positioned external to and underneath the casing to heat the water within the casing, an at least partially cylindrical separator wall within the interior space that extends downward from the casing top and toward the casing bottom to divide the interior space into a filling chamber and an annular humidification chamber that surrounds the filling chamber, and a bottom edge of the separator wall leaves a space between the separator wall and the casing bottom that defines a main passage between the filling chamber and the humidification chamber that allows the water to flow atop the casing bottom between the filling chamber and the humidification chamber, and that enables a level of the water within at least one of the filling chamber or the humidification chamber to rise high enough to block the main passage to prevent respiratory gas from passing therethrough; controlling the flow of water into the filling chamber from the water source to prevent the level of the water within at least the filling chamber from rising higher than a predetermine threshold level; and wherein at least the outer wall of the casing top and the separator wall are configured to cooperate with a surface of the water within the humidification chamber to define a pair of semi-circular elongate tube-like pathways around opposite sides of the filling chamber between the gas inlet and the gas outlet, the main flow of respiratory gas is divided into a pair of semi-circular flows of the respiratory gas that each proceed through a different one of the pair of semi-circular elongate tube-like pathways, and each semi-circular flow of the respiratory gas proceeds within its corresponding one of the pair of pathways along a corresponding one of a pair of semi-circular paths that extends generally parallel to the surface of the water within the humidification chamber to enable humidification of the respiratory gas with the water within the humidification chamber.

BRIEF DESCRIPTION OF THE DRAWINGS

A fuller understanding of what is disclosed in the present application may be had by referring to the description and claims that follow, taken in conjunction with the accompanying drawings, wherein:

FIG. 4I is another perspective view, from underneath, of the casing top thereof, and showing the paths taken by flows of respiratory gases therethrough, including the manner in which those paths are altered by the presence of the heat spreaders therealong.

DETAILED DESCRIPTION

Figure 1:
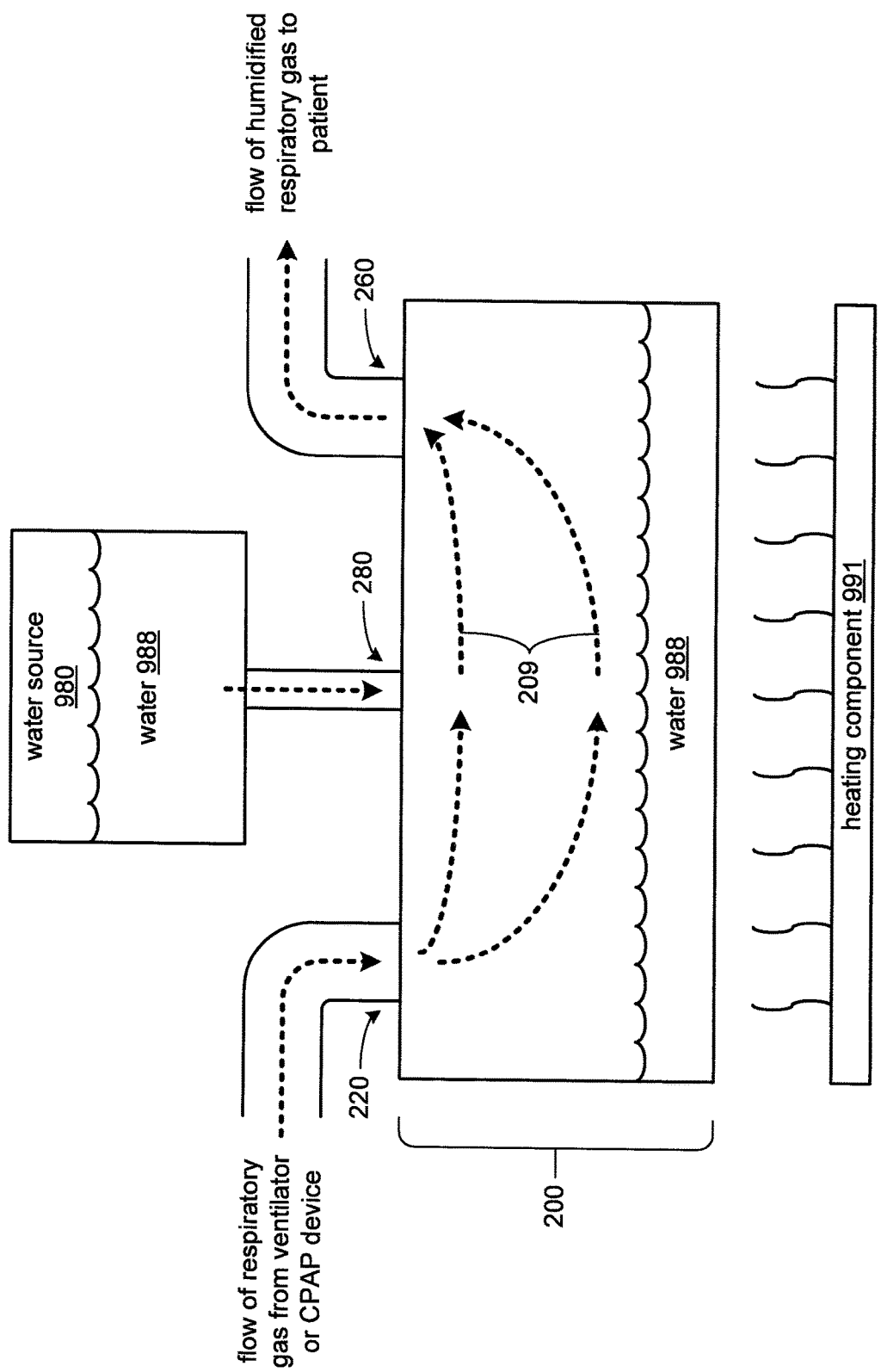
FIG. 1 is a block diagram of a PRIOR ART example of a respiratory humidification device in use to humidify respiratory gases provided to a patient.
Figure 2A:
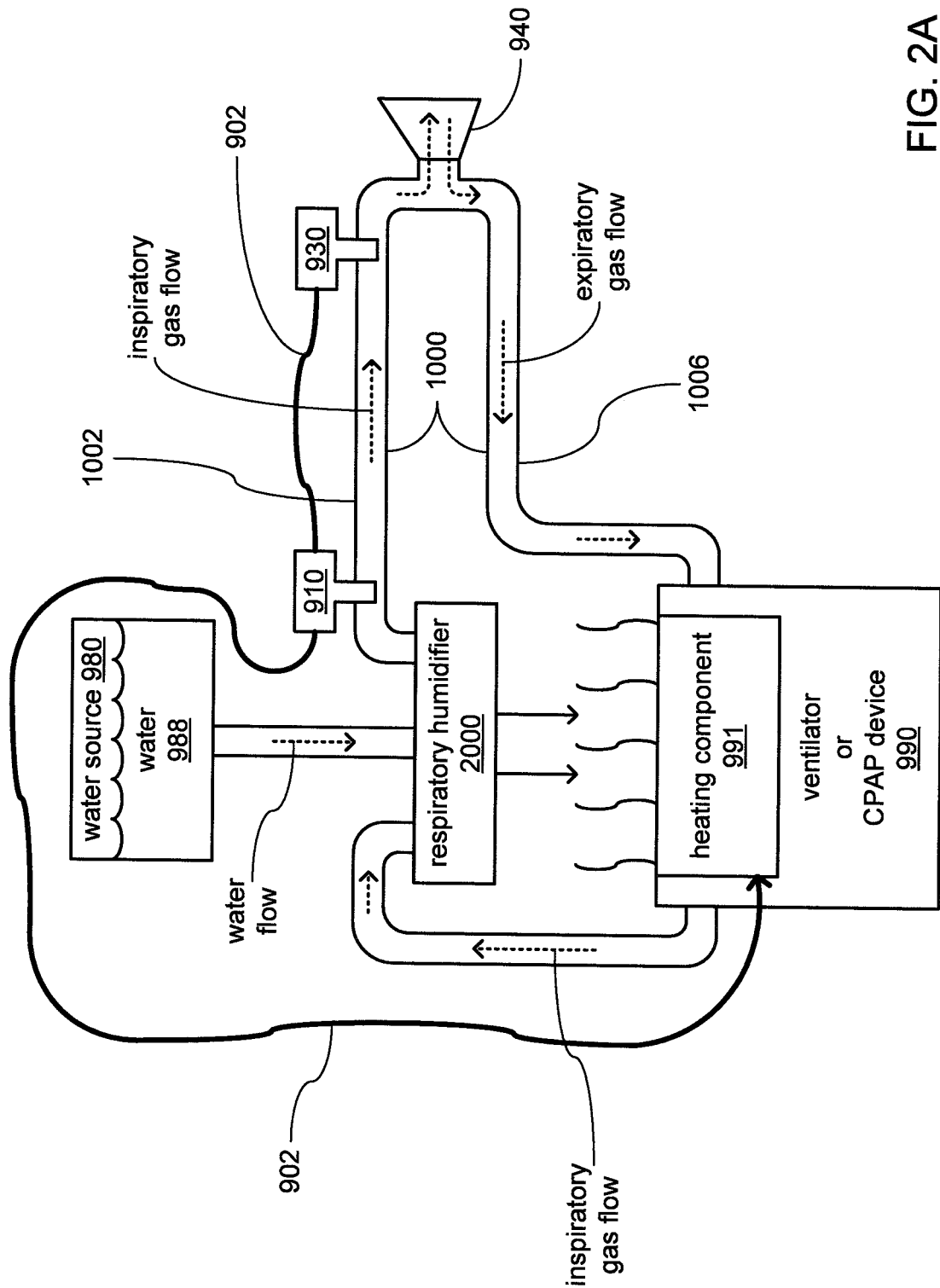
FIG. 2A is a block diagram of a novel respiratory humidification device in use to humidify respiratory gases provided to a patient, and showing details of the manner in which a depicted ventilator or CPAP device monitors temperature and flow of the respiratory gases provided to the patient using sensors, and adjusts its heating of the respiratory humidification device in response.
Figure 2B:
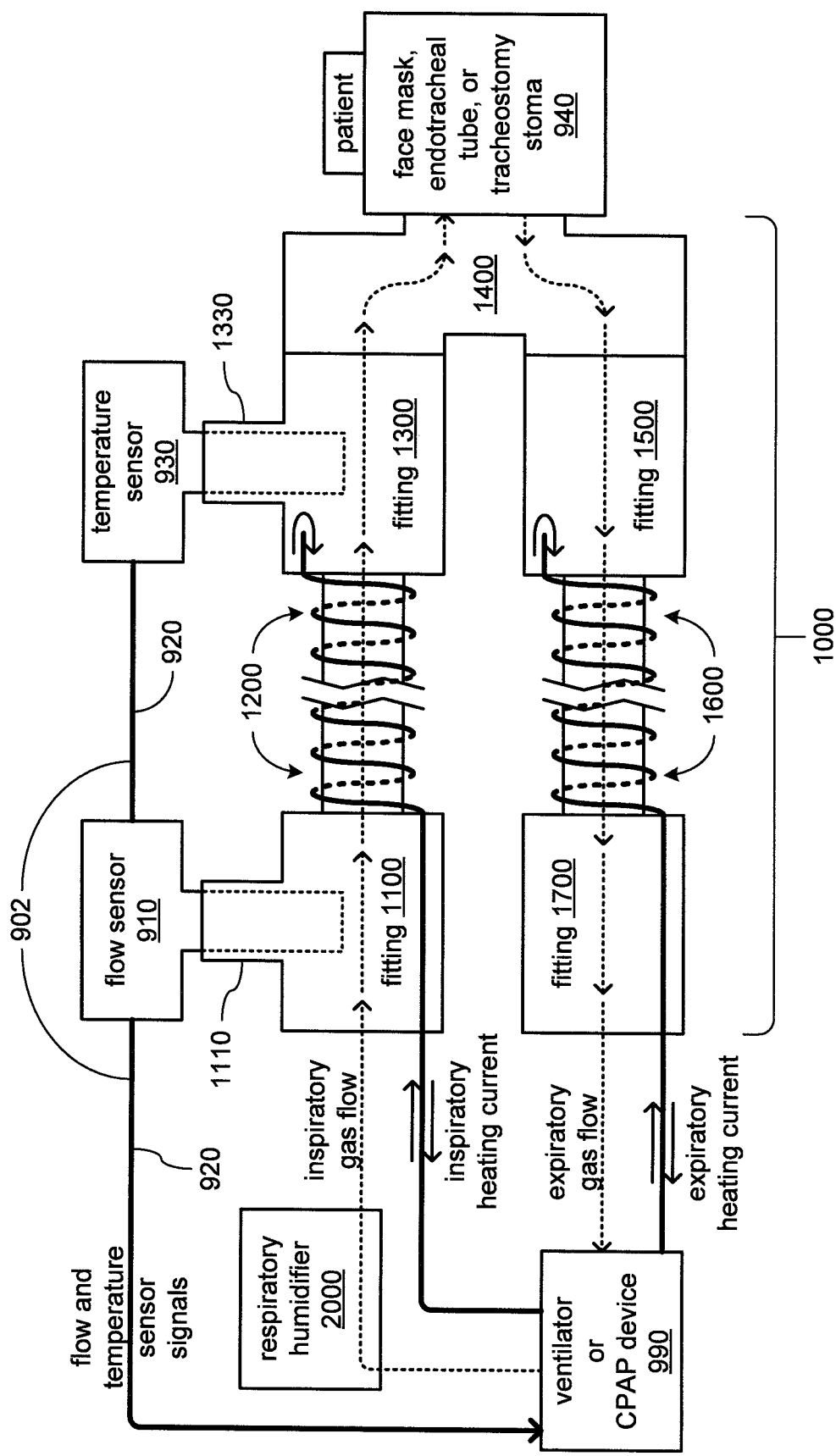
FIG. 2B is another block diagram thereof also showing the respiratory humidification device in use to humidify respiratory gases provided to a patient, and showing details of a hose assembly that conveys respiratory gases to and from the patient while supporting the placement of the sensors that monitor temperature and flow.

FIGS. 2A and 2B depict aspects of the use of a novel respiratory humidification device 2000 (which addresses many of the shortcomings of prior art respiratory humidification devices, including the prior art respiratory humidification device 200 described above) together with a ventilator or CPAP device 990, and a hose assembly 1000 to provide a patient with humidified respiratory gases to breathe. As depicted, the ventilator or CPAP device 990 provides an inspiratory gas flow of respiratory gases to a gas inlet of the respiratory humidification device 2000 to be humidified with water 988 provided to the respiratory humidification device 2000 by the water source 980.

The ventilator or CPAP device 990 may directly incorporate the heating component 991 by which the ventilator or CPAP device 990 provides heat to the respiratory humidification device 2000 to heat the water 988 and respiratory gases therein. In some embodiments, the heating component 991 may include an electrically heated hot plate atop which the respiratory humidification device 2000 may be placed to be heated in a manner akin to a pot placed atop an electric burner of a plate warmer or cooktop. As will be familiar to those skilled in the art, such provision of heat by the ventilator or CPAP device 990 to heat the water 988 and respiratory gases within the respiratory humidification device 2000 serves to both excite the molecules of the water 988 within the respiratory humidification device 2000 and increase the absorption capacity of the respiratory gases therein, thereby causing speedier and greater absorption of the water 988 into the respiratory gases.

As will shortly be explained in greater detail, within the respiratory humidification device 2000, the incoming flow of respiratory gases received at the gas inlet from the ventilator or CPAP device 990 is split into a pair of gas flows that are each directed into a tube-like pathway that is partially defined by the surface of the water 988 heated with the heat energy provided by the heating component 991. The tube-like configuration of each such pathway serves to keep its respective gas flow of respiratory gas in close contact with the surface of the water 988 to enhance the absorption of the water 988 into each gas flow. Each such tube-like pathway may follow a semi-circular path about a circular perimeter of the respiratory humidification device 2000 to elongate the path followed by each of the two gas flows to increase the amount of time that each gas flow is maintained in contact with the surface of the water 988. Each such tube-like pathway may be shaped and/or sized to encourage the formation of a vortex of the gas within its respective gas flow. The axis of each such vortex may extend along its respective pathway and generally horizontal to the surface of the water 998 to further enhance the bringing of each of the two gas flows into contact with the surface of the water 988 to further enhance absorption. The two gas flows then rejoin at a gas outlet of the respiratory humidification device 2000.

The now humidified respiratory gases are then conveyed from the gas outlet of the respiratory humidification device 2000 to a face mask, endotracheal tube or tracheostomy stoma 940 associated with a patient through an inspiratory hose assembly 1002 of a larger respiratory hose assembly 1000. In some embodiments, other respiratory gases exhaled by the patient may be conveyed back to the ventilator or CPAP device 990 through an expiratory hose assembly 1006 of the respiratory hose assembly 1000.

As depicted in greater detail in FIG. 2B, the inspiratory gas flow of humidified respiratory gases from the respiratory humidification device 2000 may be monitored by a flow sensor 910 and/or a temperature sensor 930 of a sensor harness 902. Cabling 920 of the sensor harness 902 may convey electrical and/or optical signals indicative of a detected rate of gas flow and/or of a detected temperature back to the ventilator or CPAP device 990. The flow sensor 910 may be positioned at a fitting 1100 by which the inspiratory hose assembly 1002 may be coupled to the gas outlet of the respiratory humidification device 2000 to receive the humidified respiratory gases therefrom. In contrast, the temperature sensor 930 may be positioned at a fitting 1300 by which the other end of the inspiratory hose assembly 1002 may be coupled to the face mask, endotracheal tube or tracheostomy stoma 940 of the patient through a Y-fitting 1400 to provide the respiratory gases conveyed through the hose 1200 of the inspiratory hose assembly 1002 thereto.

In embodiments in which the other respiratory gases exhaled by the patient are to be conveyed back to the ventilator or CPAP device 990, a fitting 1500 may couple the expiratory hose assembly 1006 to the Y-fitting 1400 to receive such exhaled respiratory gases therefrom. Correspondingly, a fitting 1700 may couple the other end of the expiratory hose assembly 1006 to the ventilator or CPAP device 990 to provide the exhaled respiratory gases conveyed through the hose 1600 of the expiratory hose assembly 1006 thereto.

Each of the hose assemblies 1002 and 1006 may incorporate heating wires by which each of the hoses 1200 and 1600, respectively, may be heated. As will be familiar to those skilled in the art, it may be deemed desirable to heat one or both of the hoses 1200 and 1600 to prevent the temperature of the respiratory gases conveyed therethrough from dropping low enough as to cause condensation within the hoses 1200 and 1600, respectively. Such condensation within either of the hoses 1200 or 1600 may lead to pooling of water within one or both, which may block the flow of respiratory gases therethrough. Additionally, pooling of water within the hose 1200 of the inspiratory hose assembly 1002 may create a risk of inhalation of liquid water by the patient such that drowning of the patient may occur.

Referring to both FIGS. 2A and 2B, in some embodiments, the ventilator or CPAP device 990 may use the flow rate and/or the temperature detected by the sensors 910 and/or 930, respectively, as inputs to adjust the amount of heat provided by the heating component 991, to adjust the flow of respiratory gases provided to the respiratory humidification device 2000, and/or to adjust the degree to which the wires incorporated into the hoses 1200 and/or 1600 are heated. As will be readily recognized by those skilled in the art, while the heating of the hose 1200 may serve to prevent condensation from occurring therein, the fact that the hose 1200 is "downstream" of the gas outlet of the respiratory humidification device 2000 prevents any heating of the hose 1200 from in any way assisting in the absorption of the water 998 within the respiratory humidification device 2000 into the respiratory gases that are then provided to the patient. Thus, it is to be understood that it is the heat provided by the heating component 991 of the ventilator or CPAP device 990 to the respiratory humidification device 2000 that plays a role in such the absorption of the water 988 therein.

A fuller explanation of the incorporation of heating wires into the hoses 1200 and/or 1600, as well as the use of those heating wires, may be found in each of U.S. Provisional Application 62/499,623 filed Jan. 30, 2017 by Martin E. Forrester, U.S. patent application Ser. No. 15/882,286 filed Jan. 29, 2018 by Martin E. Forrester, U.S. patent application Ser. No. 15/882,257 filed Jan. 29, 2018 by Martin E. Forrester, and U.S. patent application Ser. No. 15/882,313 filed Jan. 29, 2018 by Martin E. Forrester, all of which are incorporated herein by reference to the fullest extent that is (or may become) possible under U.S. patent law.

FIGS. 3A through 3H depict aspects of a simplified example embodiment of the novel respiratory humidification device 2000. As depicted, the respiratory humidification device 2000 has a generally cylindrical shape largely defined by a generally upstanding outer wall 2104 rising from a relatively flat casing bottom 2200 by which the respiratory humidification device 2000 may be supported atop a heating component 991 of a ventilator, CPAP device or other medical device 990 to be heated thereby. Upper portions of the outer wall 2104 may bend inwardly to form at least a portion of a casing top 2100 of respiratory humidification device 2000 integrally with the upstanding portion of the outer wall 2104. Such a circular shape of at least the casing bottom 2200 may be deemed desirable in response to the common practice of designing the heating component 991 of a ventilator, CPAP device or other medical device 990 to have a circular shape.

It should be noted that, while the casing bottom 2200 is depicted and described herein as having flat and circular shape, other embodiments of the respiratory humidification device 2000 are possible in which the casing bottom 2200 is of a different physical shape in response to physical features of the heating component 991 of a particular ventilator, CPAP device or other medical device 990. More specifically, where the heating surface provided by a particular heating component 991 is not circular in shape (e.g., has an oval or rounded rectangular shape), the casing bottom 2200 may have a corresponding or matching non-circular shape. Alternatively or additionally, where the heating surface provided by a particular heating component 991 is not flat (e.g., is convex, concave or of some other more complex shape), the casing bottom 2200 may have a corresponding or matching non-flat shape to better provide thermally-conductive contact between the casing bottom 2200 and such a heating surface. Indeed, it is envisioned that different versions of the respiratory humidification device 2000 may be fabricated to accommodate differences in physical features of the heating components 991 of various particular ventilators, CPAP devices and/or other medical devices 990 that provide respiratory gases in need of being humidified.

Referring to FIGS. 3A-D, the interior of the respiratory humidification device 2000 is divided by a generally upstanding and cylindrical separator wall 2140 into a central filling chamber 2008 and an annular humidification chamber 2004 that encircles the central filling chamber 2008. The separator wall 2140 is nested within the outer wall 2104, and may be concentric with the outer wall 2104. The separator wall 2140 at least partially defines the central filling chamber 2008, and cooperates with the outer wall 2104 to at least partially define the annular humidification chamber 2004. The casing bottom 2200 defines a common bottom of both of the chambers 2004 and 2008.

Figure 3A:
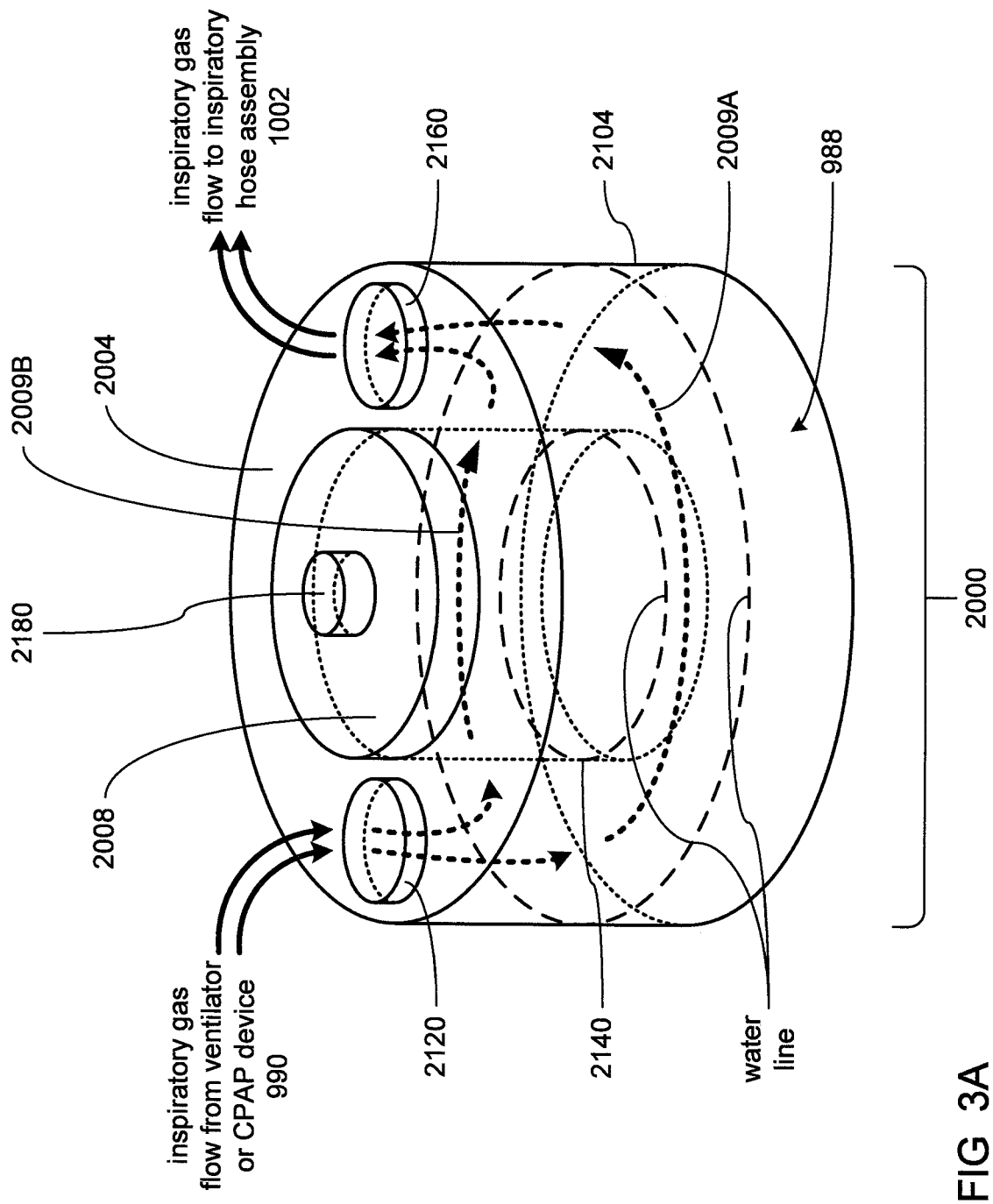
FIG. 3A is a perspective view of an example embodiment of the novel respiratory humidification device of FIGS. 2A-B showing internal structural details thereof, and showing paths taken by flows of respiratory gases therethrough.
Figure 3B:
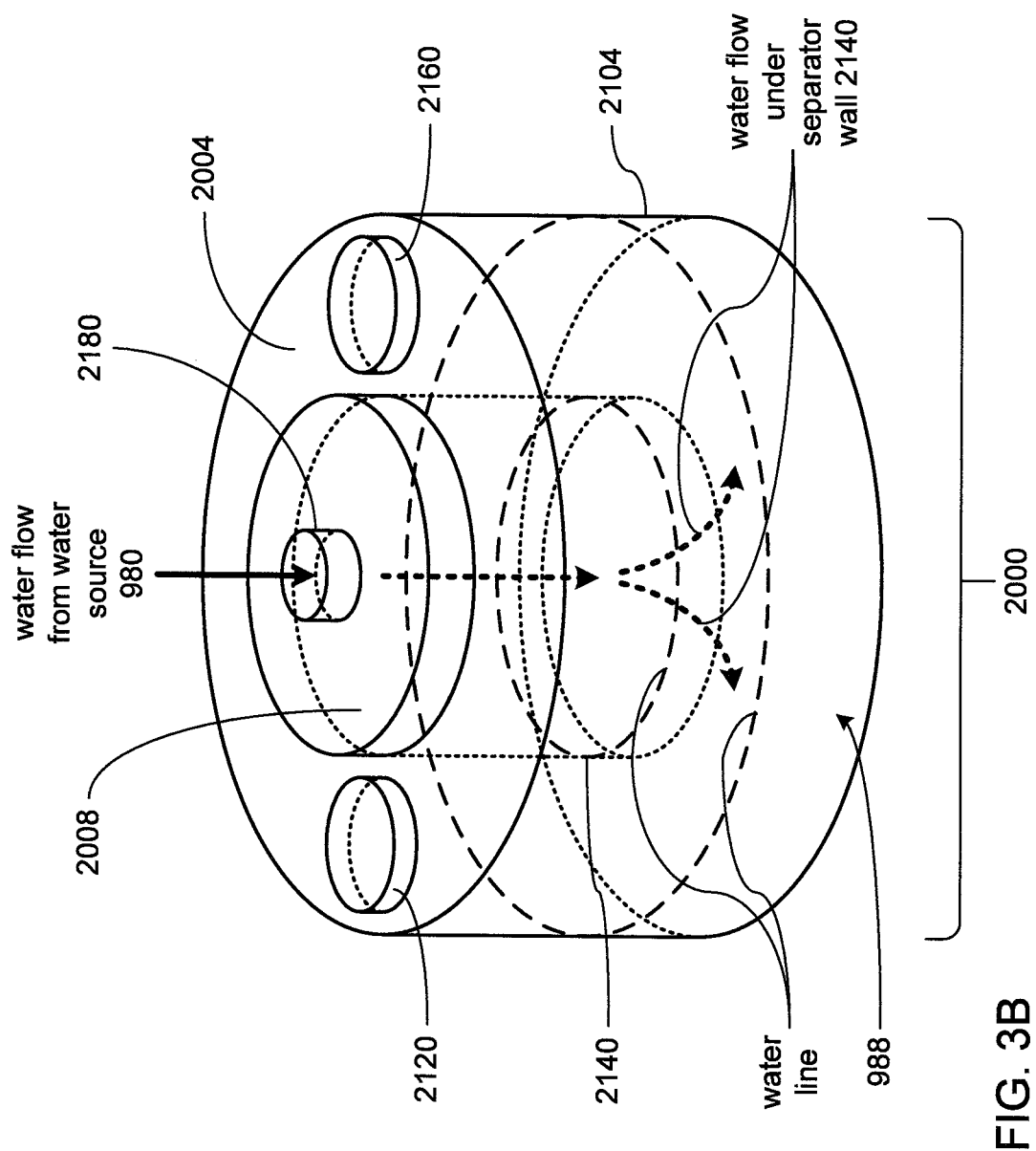
FIG. 3B is another, nearly identical, perspective view thereof showing identical internal structural details thereof, but showing the manner in which water flows therein.
Figure 3C:
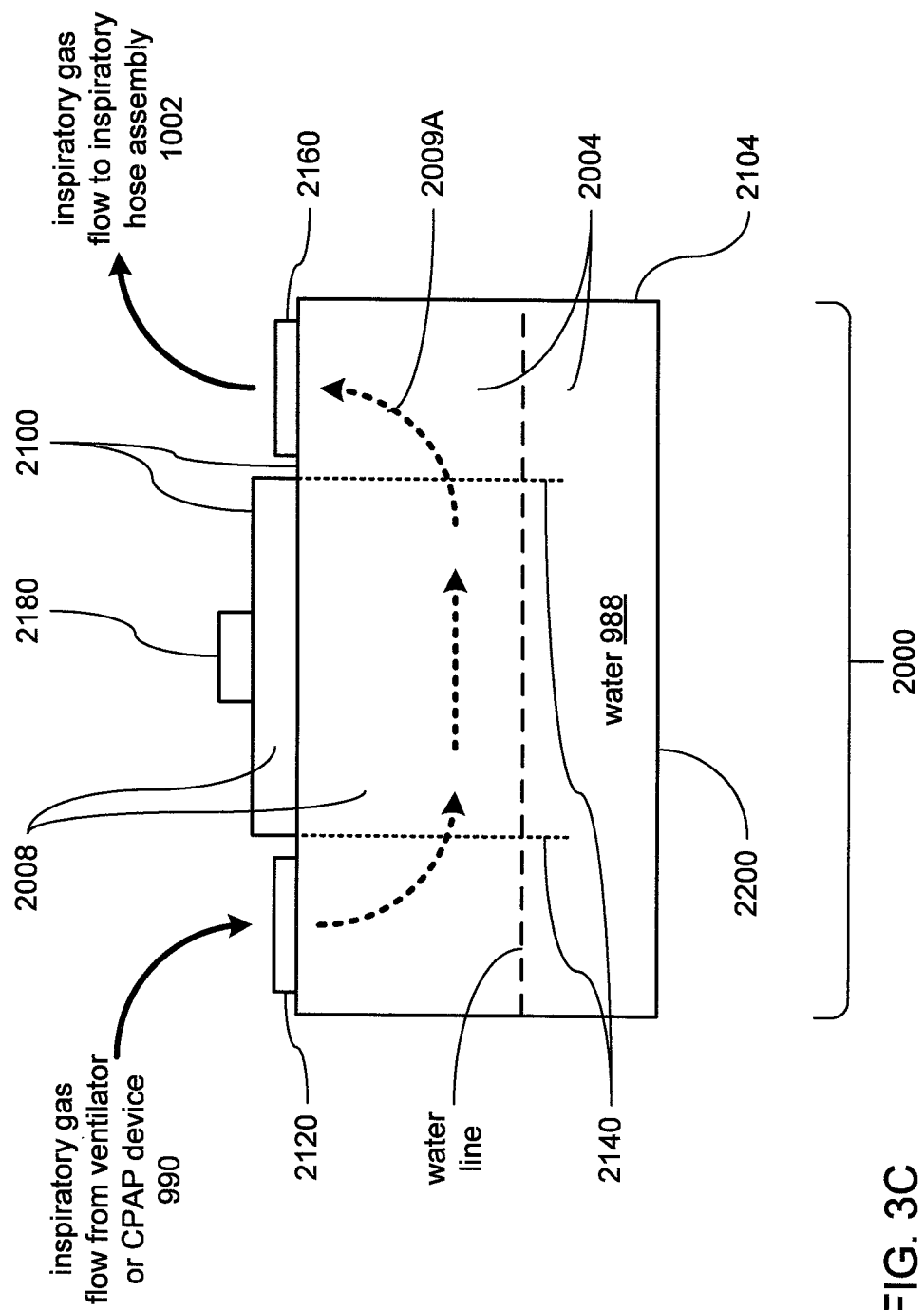
FIG. 3C is an elevational view thereof showing internal structural details thereof, and showing the paths taken by flows of respiratory gases therethrough.
Figure 3D:
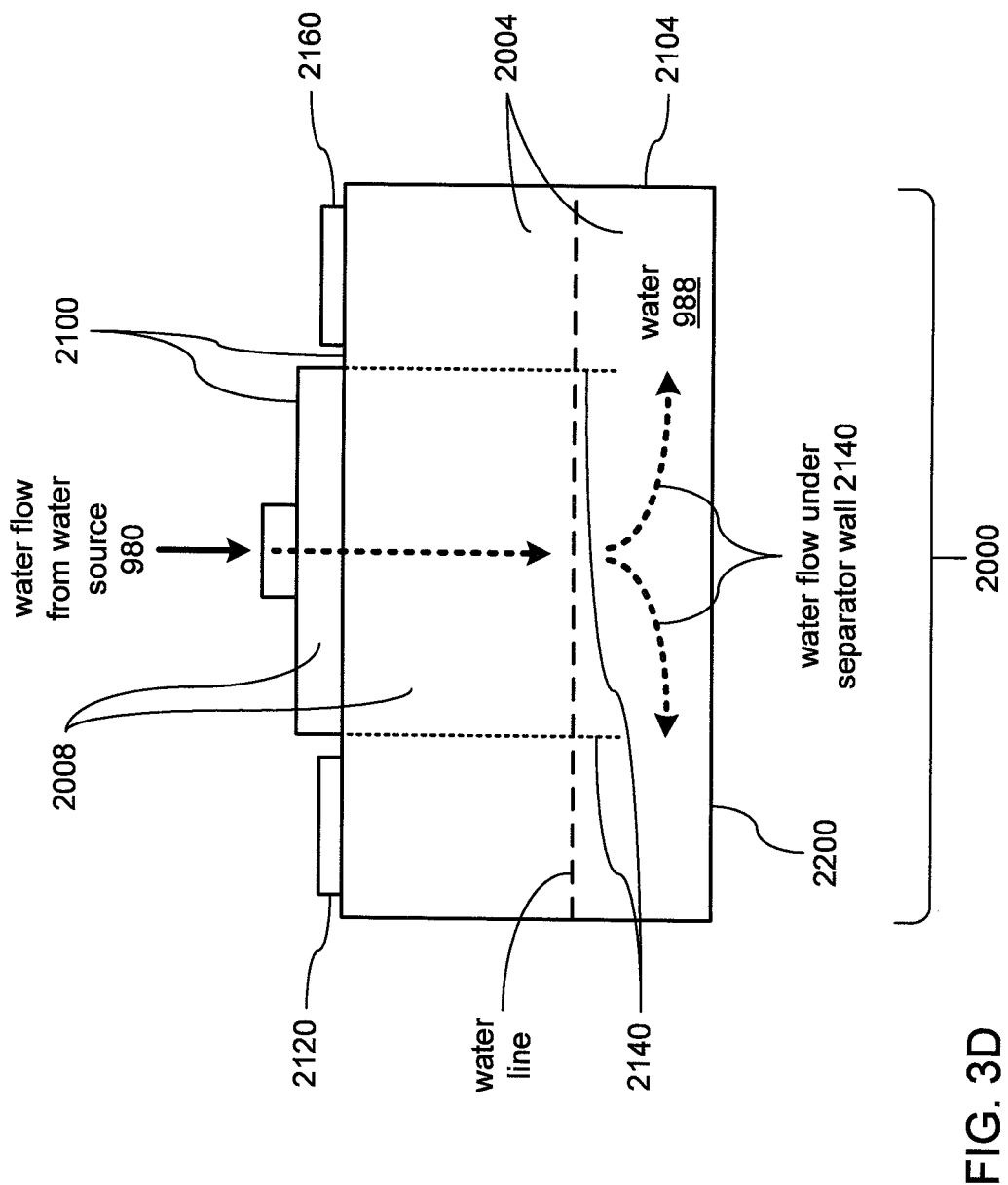
FIG. 3D is another, nearly identical, elevational view thereof showing identical internal structural details thereof, but showing the manner in which water flows therein.
Figure 3E:
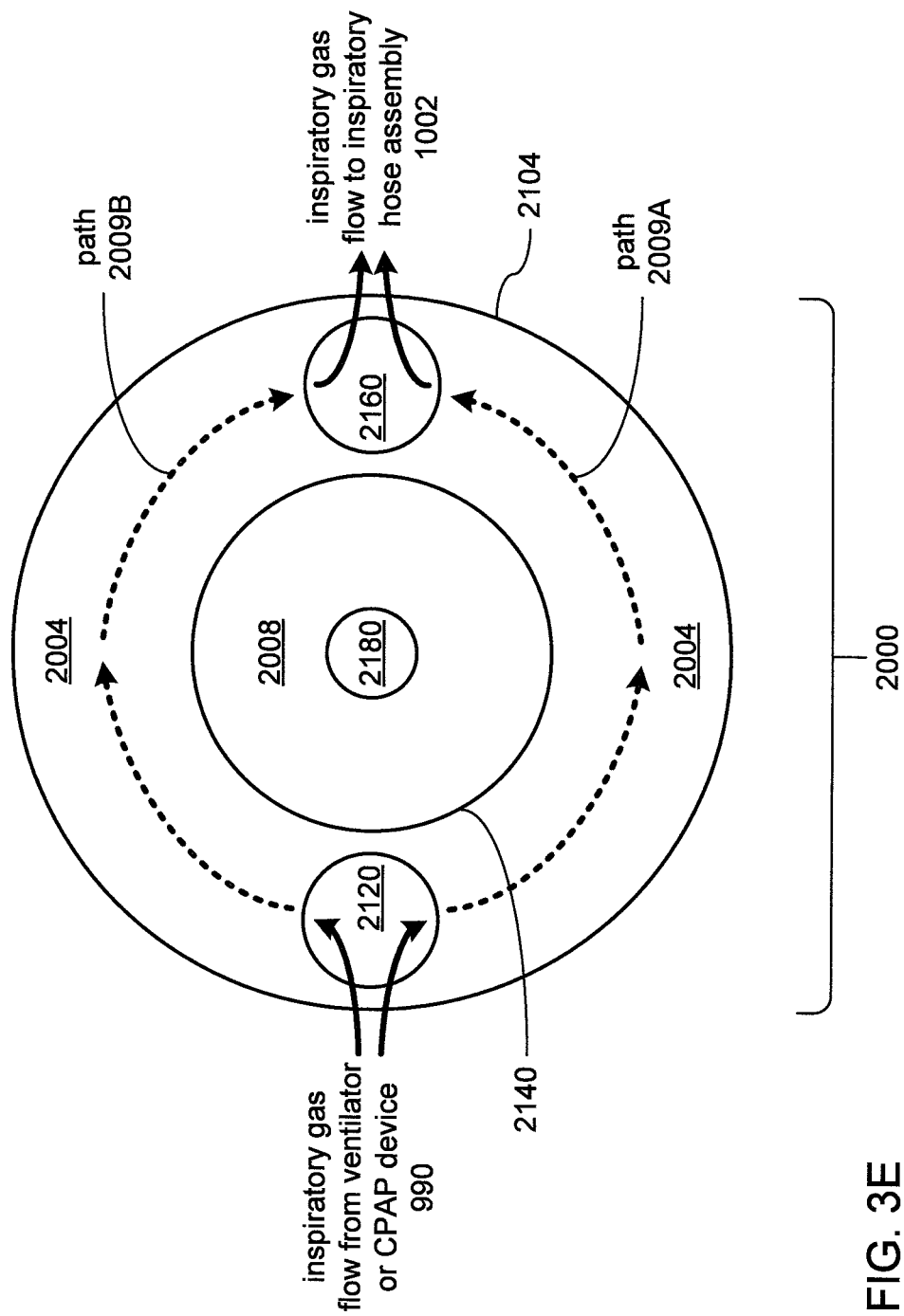
FIG. 3E is a top view thereof showing the paths taken by flows of respiratory gases therethrough.
Figure 3F:
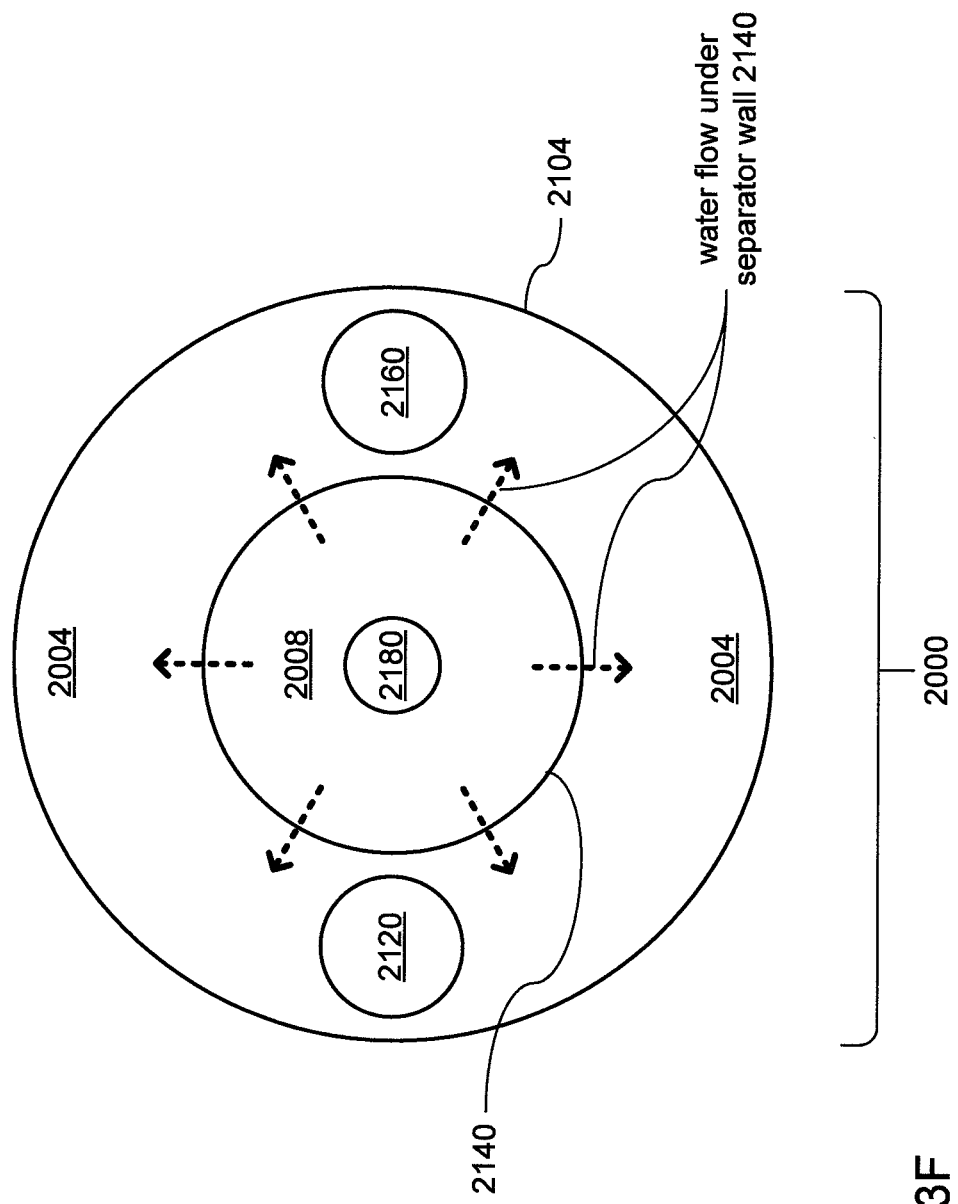
FIG. 3F is another, nearly identical, top view thereof, but showing the manner in which water flows therein.

As can be most clearly seen in FIGS. 3B and 3D, water 988 is provided from a water source (e.g., the water source 980) to the respiratory humidification device 2000 through a water inlet 2180 that opens into the central filling chamber 2008. As will be explained in greater detail, a valve incorporating a pair of floats may control the rate at which the water 988 is allowed to enter into the central filling chamber 2008 through the water inlet 2180 to control the amount of the water 988 present within the respiratory humidification device 2000.

Figure 3G:
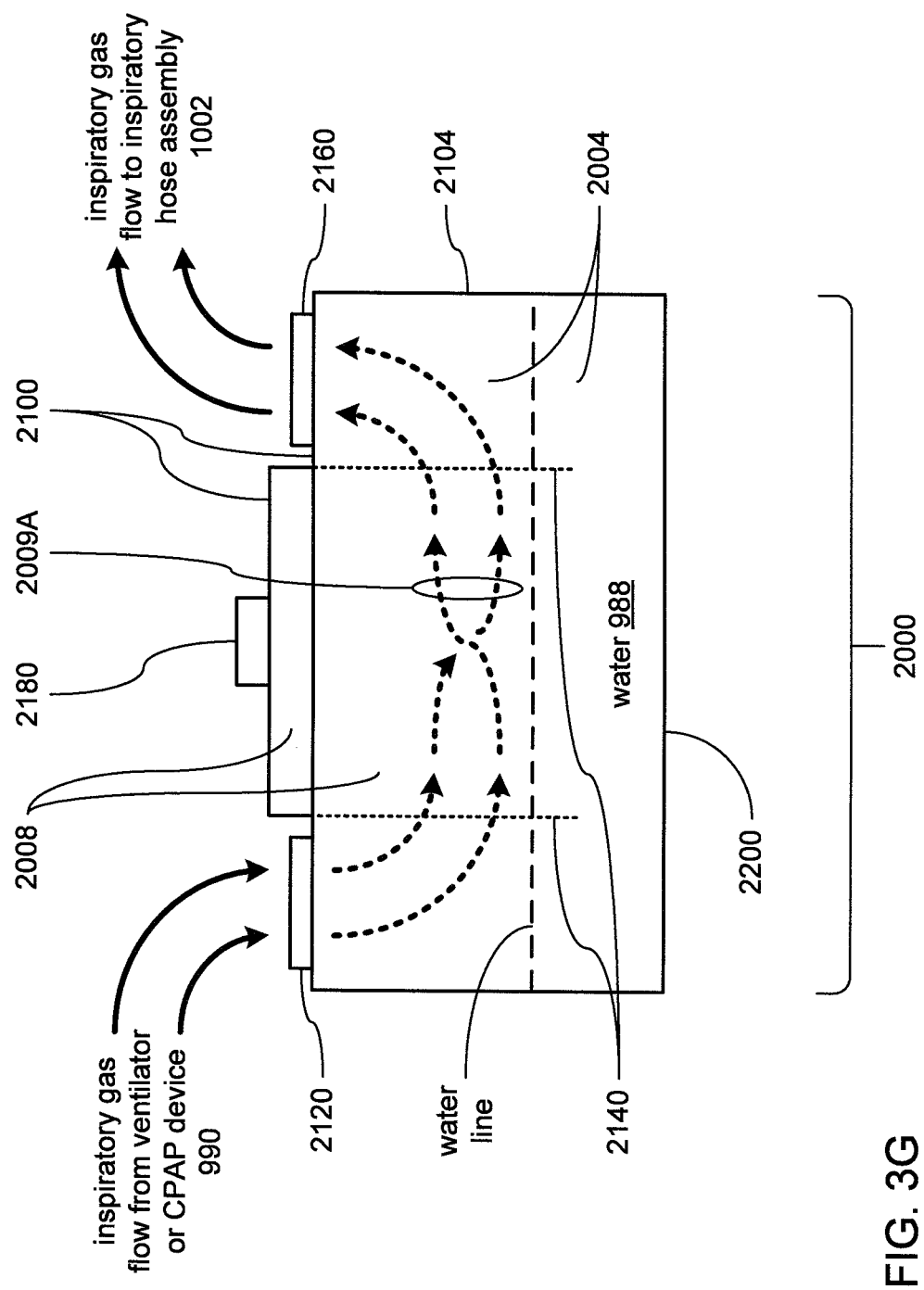
FIG. 3G is another elevational view thereof, nearly identical to FIGS. 3C-D, but showing the generation of a vortex along one of the paths taken by flows of respiratory gases therethrough.

As can be most clearly seen in FIGS. 3A-B and 3G, the two chambers 2004 and 2008 are not completely separated by the separator wall 2140. Instead, a predetermined vertical space is left between the bottom edge of the separator wall 2140 and the casing bottom 2200 to allow the water 988 that enters into the central filling chamber 2008 to flow into the annular humidification chamber 2004, as can be most clearly seen in FIGS. 3B, 3D and 3F. Thus, the water 988 is caused to pool at the bottom of both chambers 2004 and 2008, and in contact with the casing bottom 2200. As can be most clearly seen in FIGS. 3A-D and 3G, the intention is to maintain a predetermined water line of the water 988 within both chambers 2004 and 2008 of the respiratory humidification device 2000 that serves to complete the division of the chambers 2004 and 2008 from each other in a manner somewhat akin to a drain trap of a sink, where the water 988 is allowed to flow between the two chambers 2004 and 2008, but gases are not.

A flow of dry respiratory gases from a ventilator, CPAP device or other medical device is provided to the respiratory humidification device 2000 through a gas inlet 2120 that opens into the annular humidification chamber 2004. As can be most clearly seen in FIGS. 3A, 3E and 3H, near the gas inlet 2120, the incoming flow of respiratory gases is divided into a pair of semi-circular gas flows. One of the two semi-circular gas flows follows a semi-circular path 2009A within the annular humidification chamber 2004 that proceeds halfway around one side of the central filling chamber 2008. The other of the two semi-circular gas flows follows a mirror image semi-circular path 2009B within the annular humidification chamber 2004 that proceeds halfway around the other side of the central filling chamber 2008. As the two semi-circular gas flows proceed around their respective paths 2009A and 2009B, the respiratory gases of each semi-circular gas flow is urged into contact with the surface of the water at or near the water line within the annular humidification chamber 2004 to absorb molecules of the water 988, and to thereby become humidified. Both paths 2009A and 2009B meet near a gas outlet 2160 located opposite the gas inlet 2120. The now humidified and re-combined flow of respiratory gases leaves the respiratory humidification device 2000 through the gas outlet 2160 to be conveyed to a patient by an inspiratory hose assembly 1002.

As the casing bottom 2200 is heated from underneath by a heating component 991, the water 988 (which is in contact with the casing bottom 2200) is caused to be heated largely by conduction of heat through the casing bottom 2200. In turn, respiratory gases that flow over the surface of the water 988 may become heated by the water 988. Those same respiratory gases may also be heated by contact with the outer wall 2104 as a result of its contact with the casing bottom 2200, and depending on the material(s) from which the outer wall 2104 is fabricated.

As can be most clearly seen in FIGS. 3A, 3C-D and 3G, the paths 2009A and 2009B may each extend through a portion of the annular humidification chamber 2004 in which an elongate tube-like pathway is defined by the outer wall 2104 (which, as previously discussed, may also form part of the casing top 2100), the separator wall 2140, and the surface of the water 988 that fills the bottom of the annular humidification chamber 2004 up to or in the vicinity of the predetermined water line. Again, the presence of the water 988 within the annular humidification chamber 2004 at or near the predetermined water line prevents entry of the respiratory gases underneath the bottom edge of the separator wall 2140, and into or through the central filing chamber 2008, such that the water surface acts in a manner very much akin to a floor of each of the elongate tube-like pathways that the water surface aids in defining. Such use of such elongate tube-like pathways serves to constrain the paths 2009A and 2009B to extend over and parallel to the surface of the water 988, thereby tending to keep the semi-circular gas flows following each of the paths 2009A and 2009B in contact with the surface of the water 988 over a distance that has been found to be sufficient to ensure sufficient absorption of molecules of the water 988 into each of the two gas flows as to ensure that the respiratory gases leaving the respiratory humidification device 2000 are sufficiently humidified.

Figure 3H:
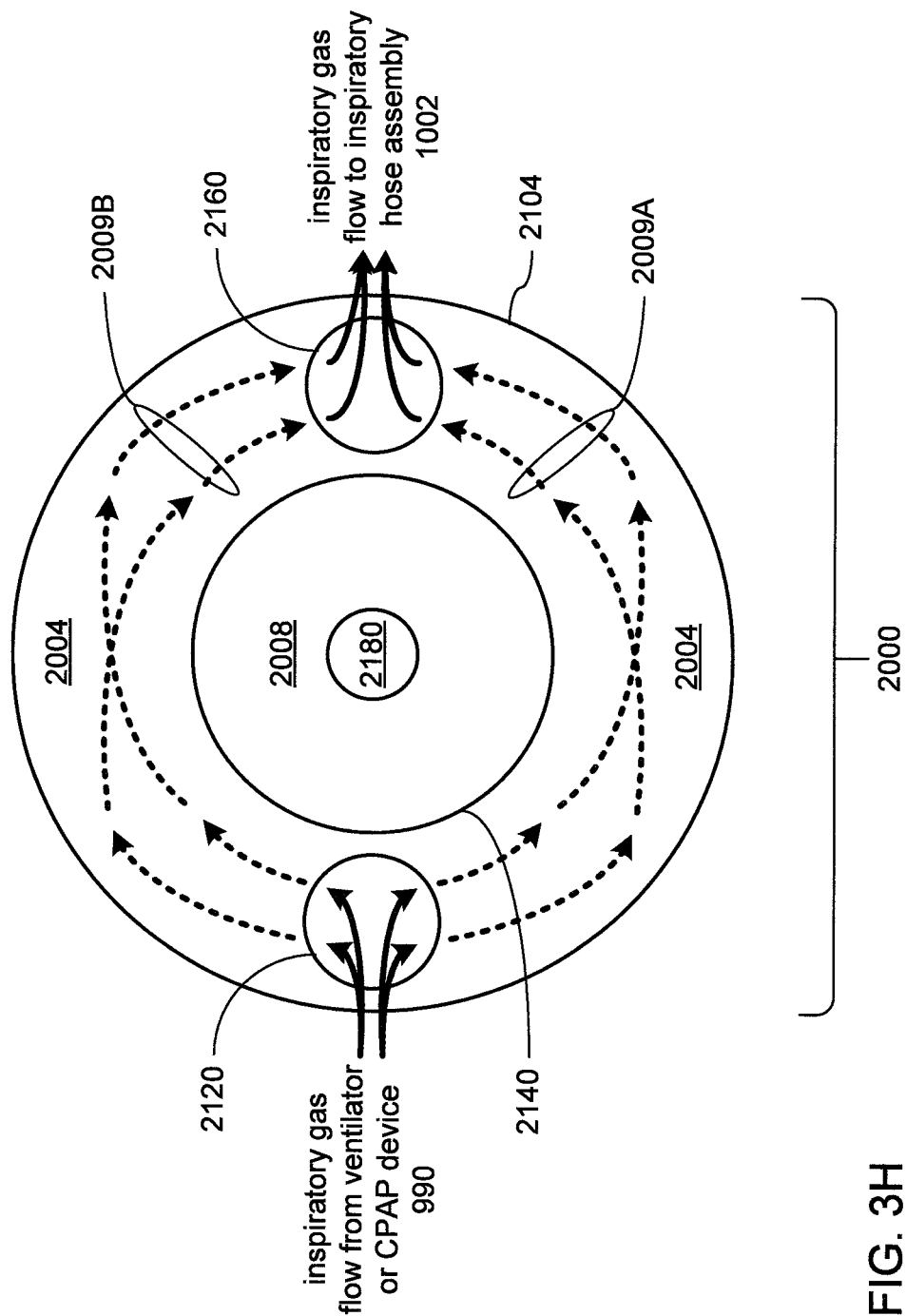
FIG. 3H is another top view thereof, nearly identical to FIGS. 3E-F, but showing the generation of a vortex along each of the paths taken by flows of respiratory gases therethrough.

As can be most clearly seen in FIGS. 3G and 3H, each of these two tube-like pathways may be shaped and sized to induce the formation of a vortex along each of the paths 2009A and 2009B. Each such vortex may be caused to extend generally horizontally (i.e., parallel to the plane of the surface of the water 988), and may serve to ensure that a greater portion of the respiratory gases within each of the two semi-circular gas flows is put into contact with the surface of the water 988 to thereby provide more opportunity for the absorption of the water 988.

As the water 988 within the annular humidification chamber 2004 is absorbed into the two semi-circular flows of respiratory gases therethrough, the water 988 therein is replenished from the central filling chamber 2008 through the space between the bottom edge of the separator wall 2140 and the casing bottom 2200. In turn, the water 988 within the central filling chamber 2008 is replenished through the water inlet 2180. As will be explained in greater detail, the earlier-mentioned pair of floats within the central filling chamber 2008 serve to limit the amount of the water 988 that is allowed to flow in through the water inlet 2180 to what is needed to replenish the water within the respiratory humidification device 2000 to a degree sufficient to maintain the surfaces of the water 988 within both of the chambers 2004 and 2008 at or near the predetermined water line.

It should be noted that, while the respiratory humidification device 2000 is depicted and described herein as having a distinct gas inlet 2120 through which respiratory gases enter to be humidified, and a distinct gas outlet 2160 though which humidified respiratory gases leave the respiratory humidification device 2000; in at least some embodiments, the gas inlet 2120 and the gas outlet 2160 may be physically identical, and at least the internal physical design of the respiratory humidification device 2000 (if not also the external physical design) may be sufficiently physically symmetrical between the portion that includes the gas inlet 2120 and the portion that includes the gas outlet 2160, that respiratory gases may be made to flow through the respiratory humidification device 2000 in either direction between the gas inlet 2120 and the gas outlet 2160 without any change in the effectiveness of the humidification of those respiratory gases. Stated differently, in such embodiments, it may make no functional difference, whatsoever, whether the gas inlet 2120 and the gas outlet 2160 are used as has been described, or are used in a manner in which their roles are reversed such that respiratory gases flow through the respiratory humidification device 2000 in the opposite direction from what is described herein. This may be deemed a desirable feature as a form of "failsafe" against instances in which the respiratory humidification device 2000 is inadvertently connected "backwards" to a combination of the respiratory hose assembly 1000, and a ventilator, CPAP device or other respiratory device 990.

FIGS. 4A through 4I depict aspects of a more detailed example embodiment of the respiratory humidification device 2000. As best seen in FIGS. 4A-B, again, the exterior of the respiratory humidification device 2000 is formed from a casing top 2100 (which may include the outer wall 2104) and the casing bottom 2200. In at least some embodiments, the casing bottom 2200 may be formed from any of a variety of metals and/or other materials capable of conducting heat applied to the casing bottom 2200 by a ventilator, CPAP device or other medical device 990 into both the annular humidification chamber 2004 and the central filling chamber 2008. In contrast, the casing top 2100 may be formed from any of a variety of plastics and/or other materials capable of acting as thermal insulators to aid in keeping, within the respiratory humidification device 2000, the heat that is conveyed into the chambers 2004 and 2008 of the respiratory humidification device 2000 through the thermally conductive casing bottom 2200. Any of a variety of bonding, welding, and/or other techniques for coupling materials in a manner that forms a watertight seal may be used to join the casing top 2100 to the casing bottom 2200 about their peripheries.

In some embodiments, the respiratory humidification device 2000 may be intended to be discarded after being used for a predetermined period of time that may be selected to limit the degree to which bacteria and/or other microbial contaminants are allowed to take hold within the interior of the respiratory humidification device 2000 before it is discarded and replaced within another one. In such disposable embodiments, the casing top 2100 may be formed of a relatively inexpensive thermally insulating plastics material such as polystyrene, and the casing top 2200 may be formed of a relatively inexpensive thermally conductive metal such as aluminum.

As with the respiratory humidification device 2000 of FIGS. 3A-H, the respiratory humidification device 2000 of FIGS. 4A-I may have a generally cylindrical shape with the outer wall 2104 of the casing top 2100 rising vertically with a cylindrical shape from the relatively flat casing bottom 2200. Again, upper portions of the outer wall 2104 may bend inwardly to form at least a portion of the top of respiratory humidification device 2000 integrally with the upstanding portion of the outer wall 2104, at least for the portions of the annular humidification chamber 2004 that extend between the gas inlet 2120 and the gas outlet 2160. Again, such a circular shape of at least the casing bottom 2200 may be deemed desirable in response to the common practice of designing the heating components 991 of a ventilator, CPAP device or other medical device 990 to have a circular shape.

Figure 4A:
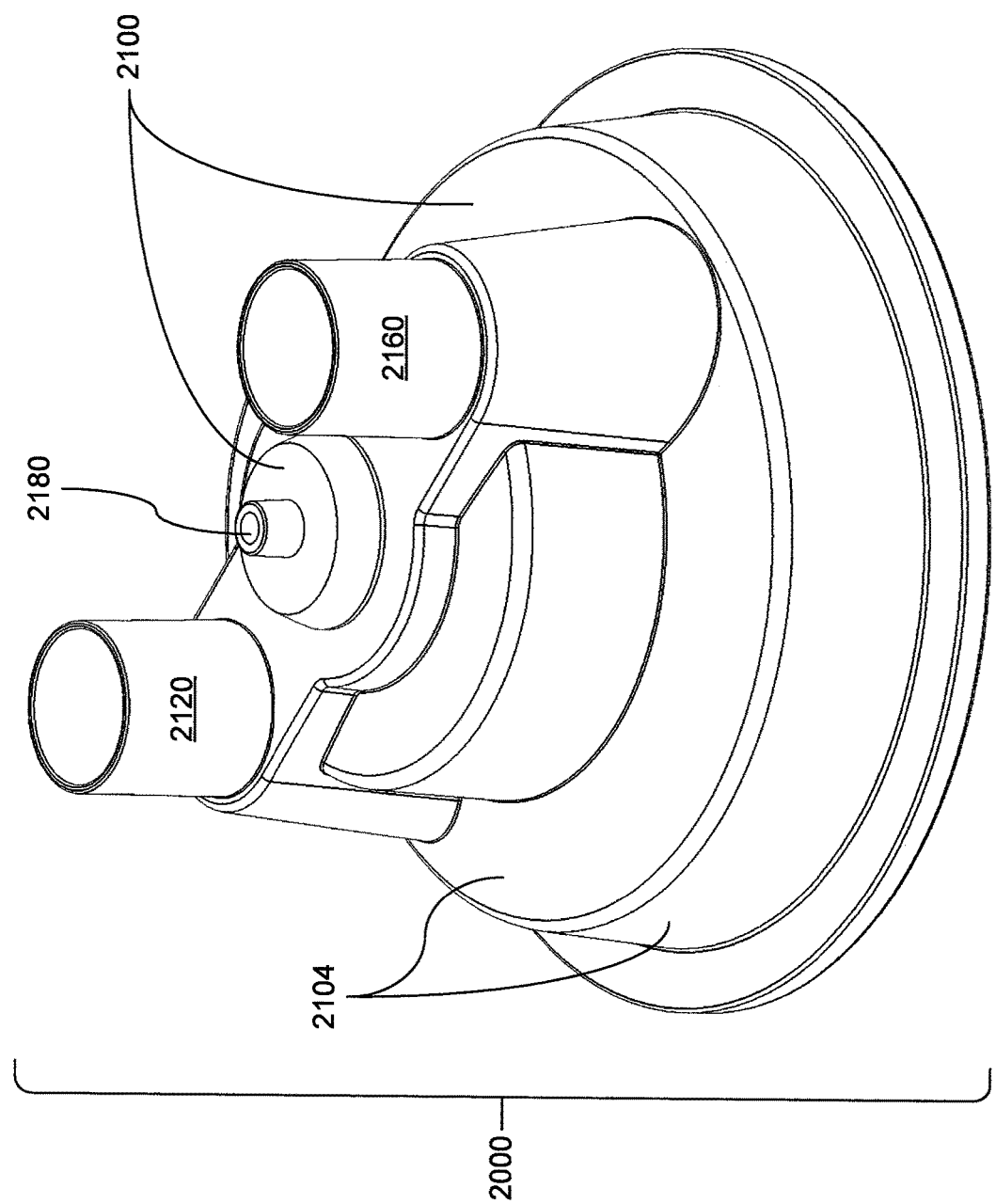
FIG. 4A is a perspective view of another example embodiment of the novel respiratory humidification device of FIGS. 2A-B showing external details of a casing top thereof.
Figure 4B:
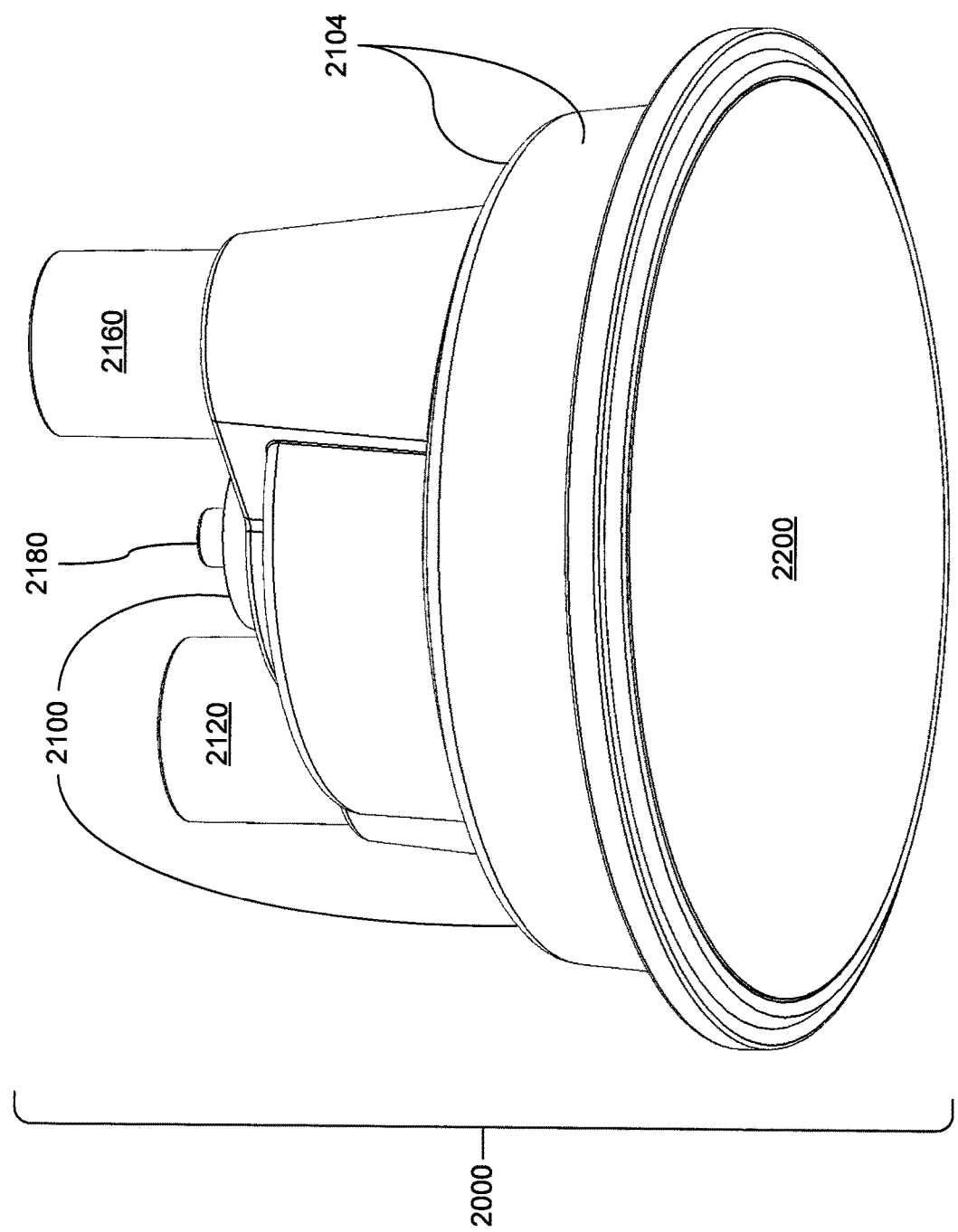
FIG. 4B is another perspective view thereof showing external details of a casing bottom thereof.
Figure 4C:
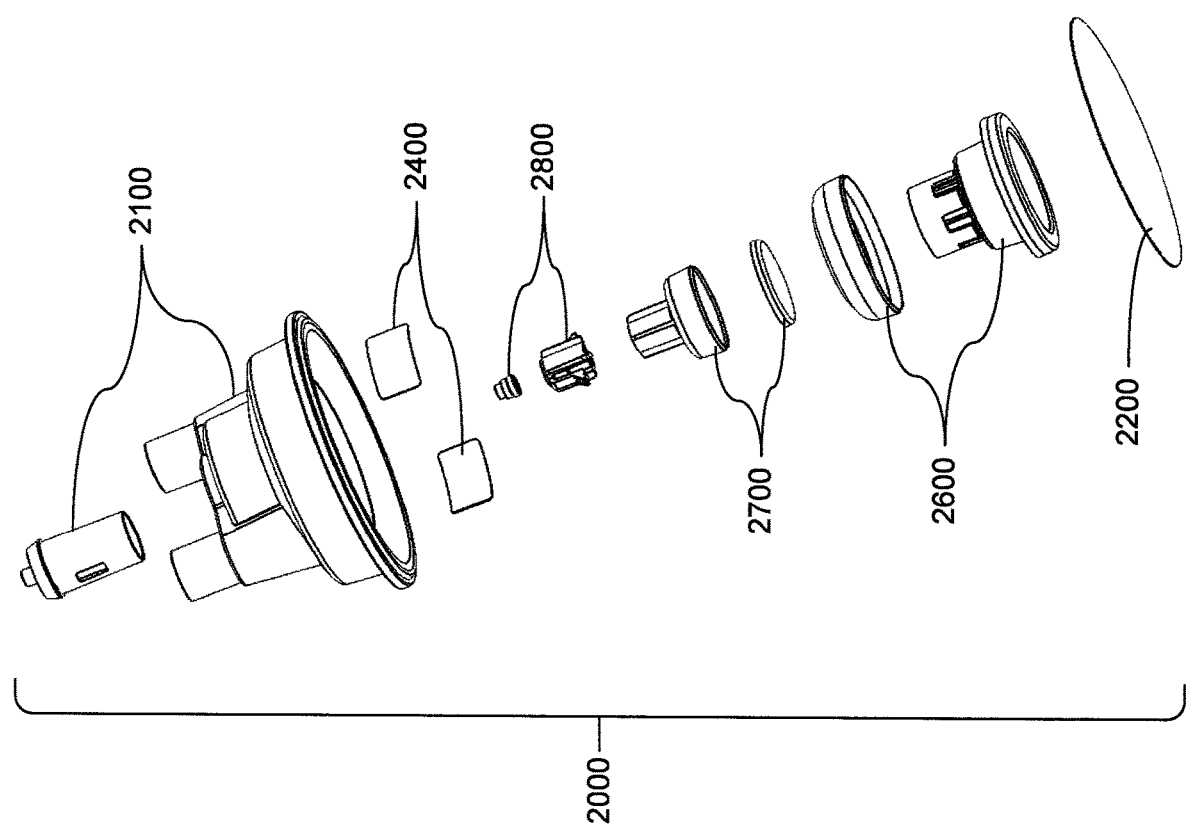
FIG. 4C is an exploded perspective view thereof showing components of both the casing top, as well as a pair of heat exchangers, and components of a valve and of a pair of floats therein.

Turning more specifically to FIG. 4C, in addition to the casing top 2100 and the casing bottom 2200, embodiments of the respiratory humidification device 2000 may include a valve 2800, a large float 2600 and a small float 2700 that may cooperate to perform the earlier-described function of limiting the amount of the water 988 that enters the respiratory humidification device 2000 through the water inlet 2180. Alternatively or additionally, embodiments of the respiratory humidification device 2000 may include a pair of heat exchangers 2400. As will be explained in greater detail, each of the pair of heat exchangers 2400 may be disposed along one of the paths 2009A and 2009B to enhance the heating of the respiratory gases flowing therealong. As also depicted in FIG. 4C, in various embodiments, one or more of the depicted components may be formed as multiple parts that are formed separately and subsequently combined. Thus, as can be seen, each of the casing top 2100, the large float 2600, the small float 2700 and/or the valve 2800 may be so formed from multiple parts.

Turning more specifically to FIG. 4D, again, the interior of the respiratory humidification device 2000 is divided into the central filling chamber 2008 and the annular humidification chamber 2004 by the separator wall 2140. However, once again, and as best seen in FIGS. 4E-H, the separator wall 2140 does not fully separate the two chambers 2004 and 2008, and instead, a predetermined vertical space is left between the bottom edge of the separator wall 2140 and the casing bottom 2200 to allow the water 988 that enters into the central filling chamber 2008 to flow through that space and into the annular humidification chamber 2004. As also depicted in FIG. 4D, in embodiments in which the casing top 2100 is formed from more than one part, the upper-most surface of the casing top 2100 may have a valve guide aperture 2108 formed therethrough to receive a separate part of the casing top 2100 that carries and/or guides the movement of the valve 2800, as well as of the floats 2600 and/or 2700, as will be explained in greater detail.

Turning more specifically to FIGS. 4D-F, again, a flow of dry respiratory gases from a ventilator, CPAP device or other medical device 990 are provided to the respiratory humidification device 2000 through the gas inlet 2120 that opens into the annular humidification chamber 2004. Near the gas inlet 2120, the incoming flow of respiratory gases is divided into a pair of semi-circular gas flows that each follow one of the paths 2009A and 2009B. As the two semi-circular gas flows proceed around their respective paths 2009A and 2009B, the respiratory gases of each are urged into contact with the surface of the water 988 at or near the water line within the annular humidification chamber 2004 to absorb water molecules thereof, and to thereby become humidified. The two semi-circular gas flows meet and rejoin near the gas outlet 2160 located opposite the gas inlet 2120, and the now humidified and re-combined flow of respiratory gases leaves the respiratory humidification device 2000 through the gas outlet 2160 to be conveyed to a patient.

Figure 4D:
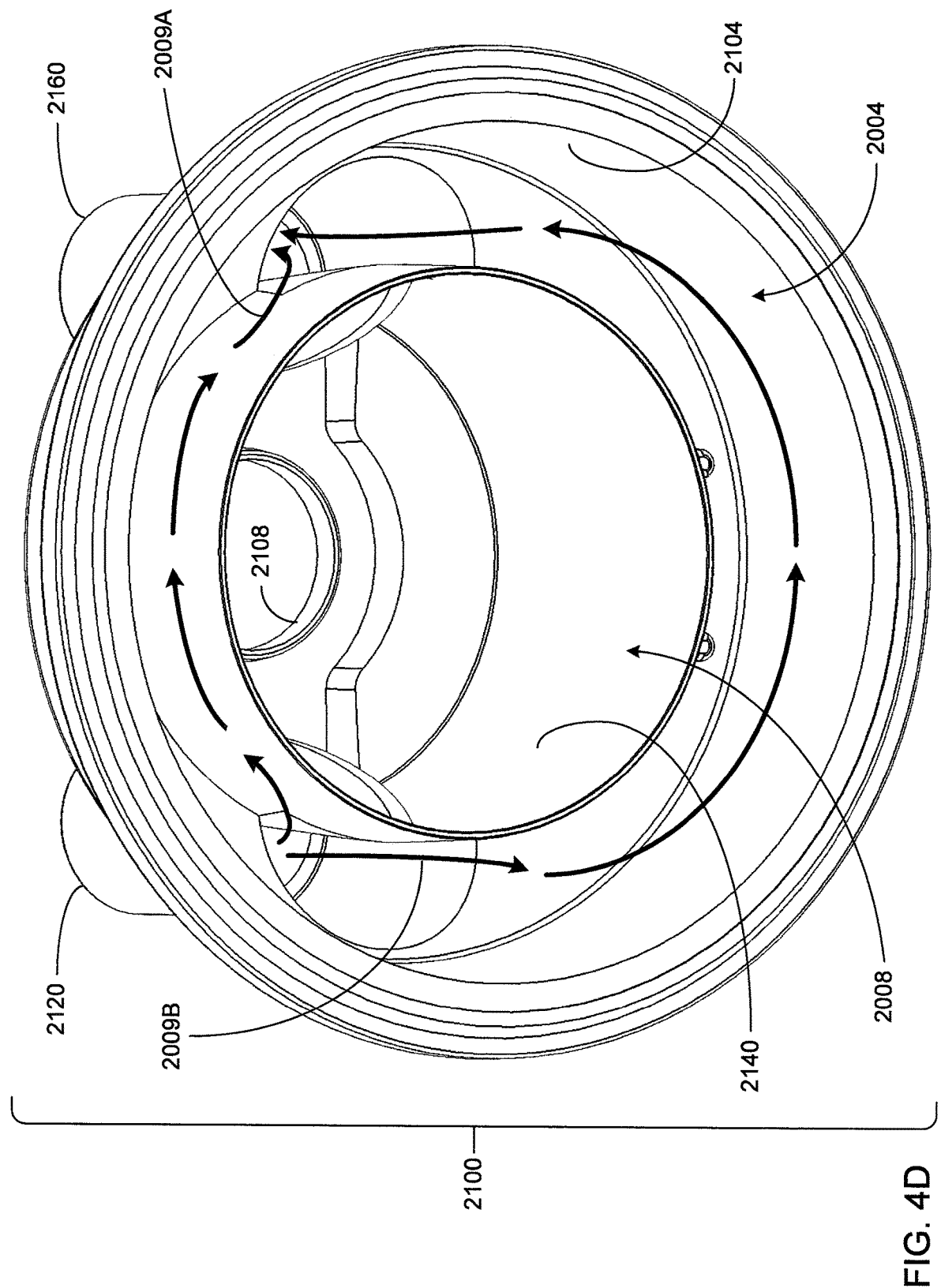
FIG. 4D is a perspective view, from underneath, of the casing top thereof, and showing the paths taken by flows of respiratory gases therethrough.
Figure 4E:
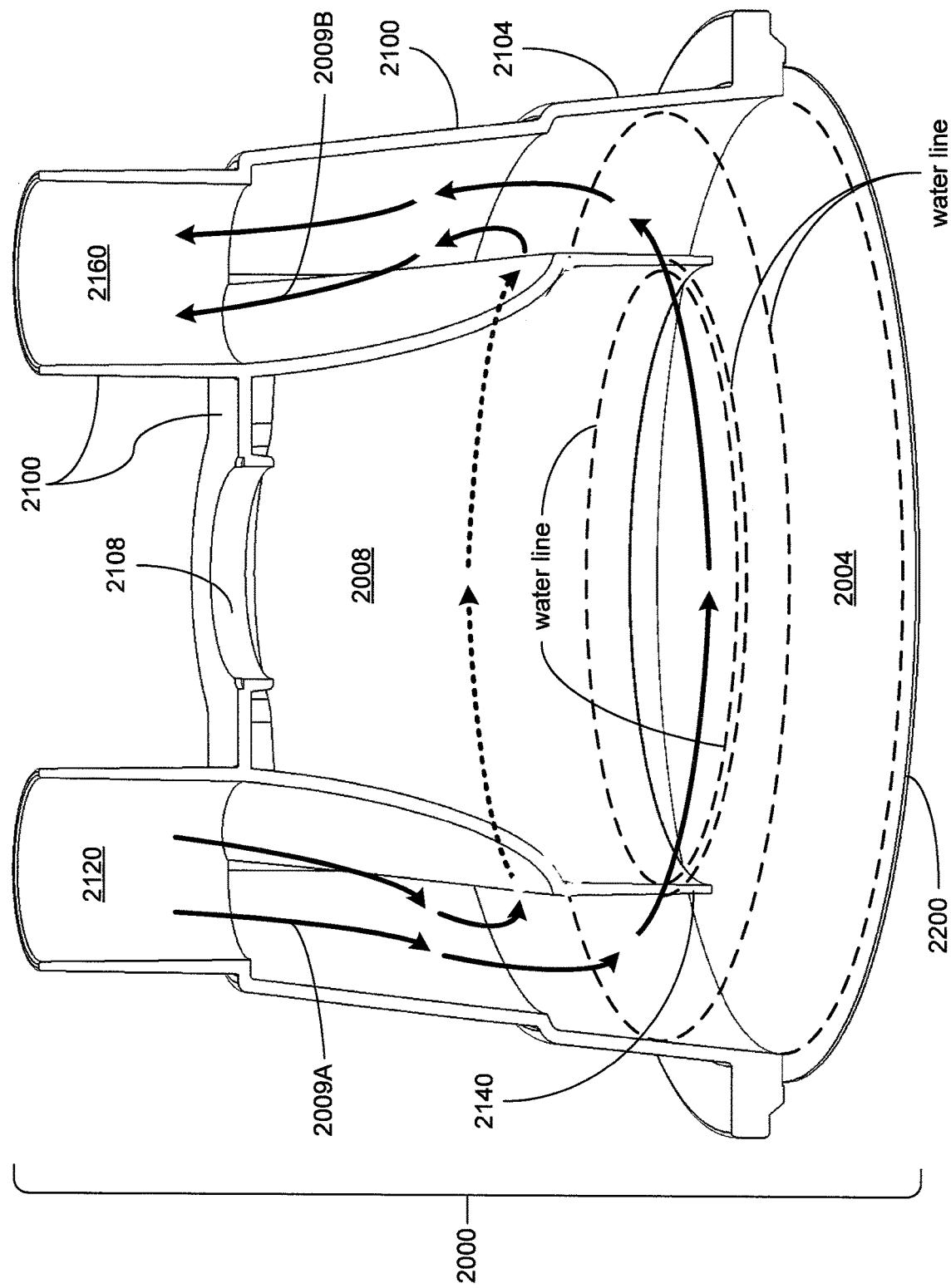
FIG. 4E is another perspective view of the same novel humidification device with a complete casing bottom, but with half of the casing top cut away along a sectional plane that cuts through both a gas inlet and a gas outlet of the casing top, and showing the paths taken by flows of respiratory gases therethrough.
Figure 4F:
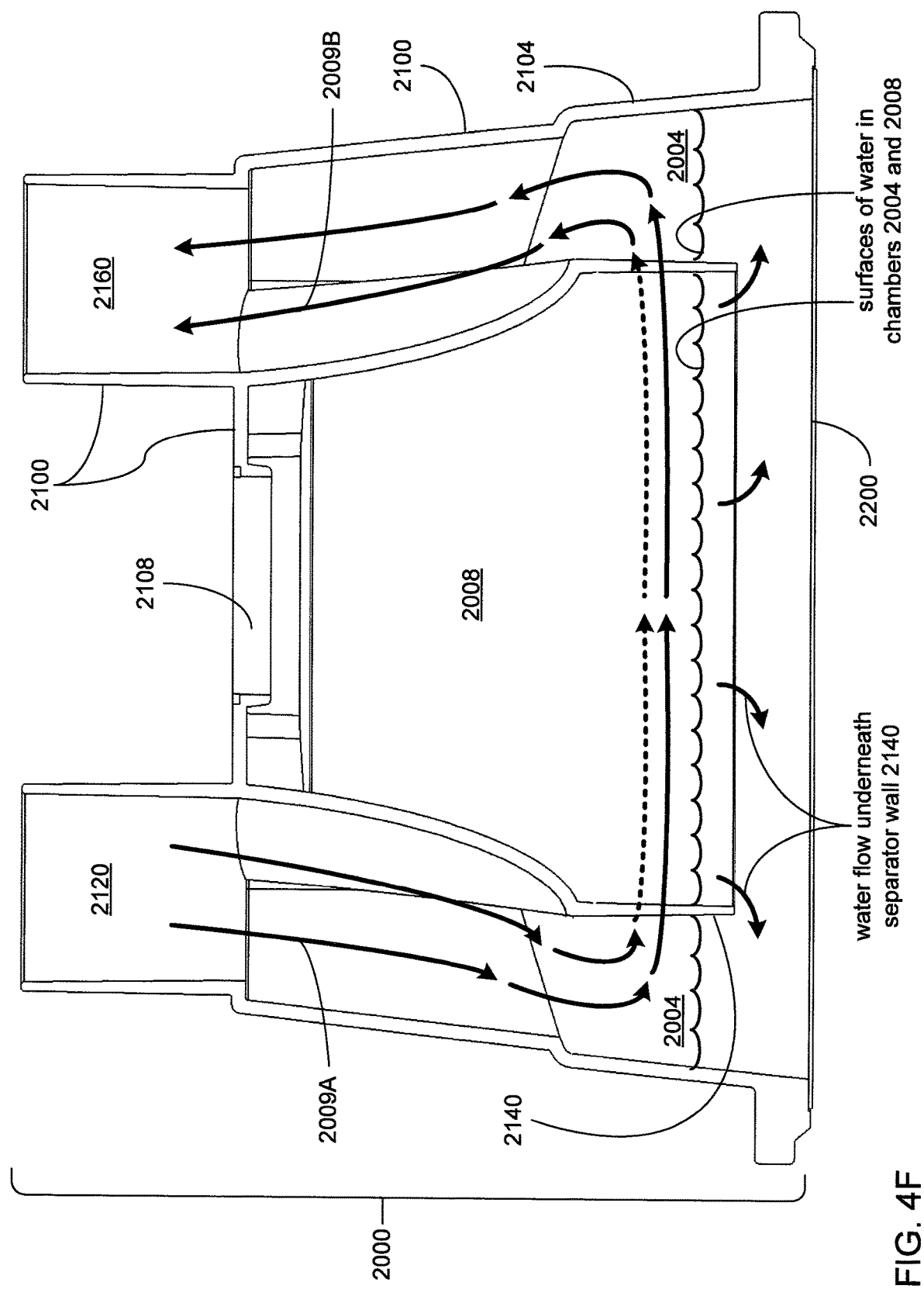
FIG. 4F is an elevational view thereof, also with a complete casing bottom and half of the casing top cut away along a sectional plane that again cuts through both the gas inlet and gas outlet, and showing the paths taken by flows of respiratory gases therethrough, as well as additionally depicting a water level of the water to be maintained therein during humidification of the respiratory gases that flow therethrough.

FIG. 4D provides a view (from underneath the open bottom of the casing top 2100) of the manner in which each of the paths 2009A and 2009B extend in a semi-circular manner around the separator wall 2140, and thereby, extend around the central filling chamber 2008. Each of FIGS. 4E-F provide a sectional view (one in perspective, the other in elevation) in which half of the casing top 2100 is cut away (but, in which the casing bottom 2200 is not cut away) to reveal portions of the paths 2009A (which loops in a semi-circle out of and back into the page around the central filling chamber 2008) and 2009B (which extends around behind the central filling chamber 2008). FIG. 4E more clearly depicts the separate water lines of the water within each of the chambers 2004 and 2008. As shown, it may be deemed desirable for the water levels within each of the chambers 2004 and 2008 to remain the same or at least relatively similar.

Turning more specifically to FIGS. 4G-H, again, the paths 2009A and 2009B may each extend through a portion of the annular humidification chamber 2004 in which an elongate tube-like pathway is defined by the outer wall 2104 (which, again, may also bend inwards to define at least part of the top surface of the casing top 2100), the separator wall 2140, and the water that fills the bottom of the annular humidification chamber 2004 up to, or in the vicinity of the predetermined water line. Again, such use of such elongate tube-like pathways serves to constrain the paths 2009A and 2009B to extend over and parallel to the surface of the water 988, thereby tending to keep the two semi-circular gas flows following each of the paths 2009A and 2009B in contact with the surface of the water 988 over an elongated distance that has been found to be sufficient to ensure sufficient absorption of molecules of the water 988 into the respiratory gases.

Figure 4G:
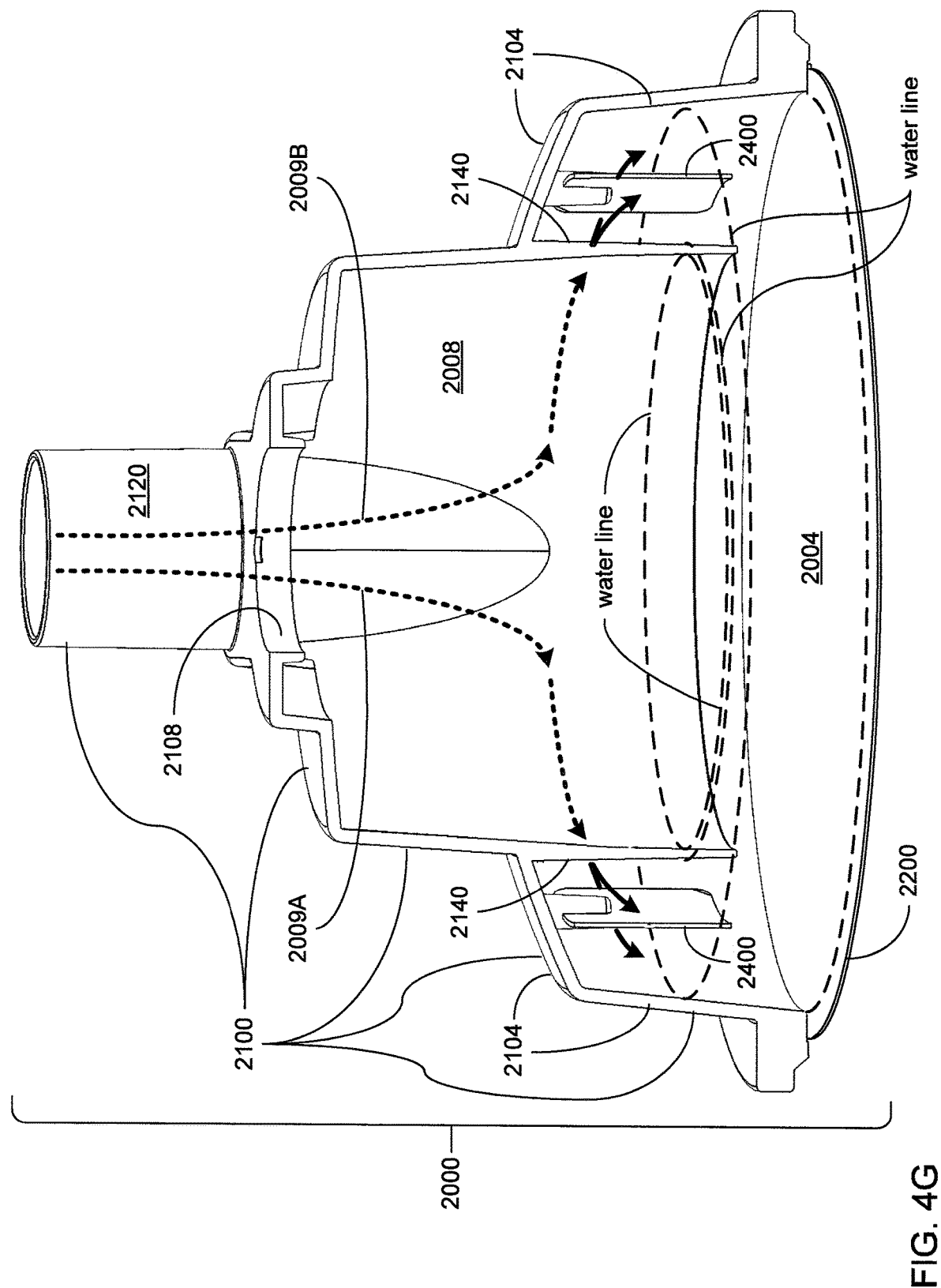
FIG. 4G is another perspective view of the same novel humidification device with a complete casing bottom, but with half of the casing top cut away along a sectional plane that cuts through the casing top at a location between the gas inlet and gas outlet, and showing part of each of the paths taken by flows of respiratory gases therethrough.
Figure 4H:
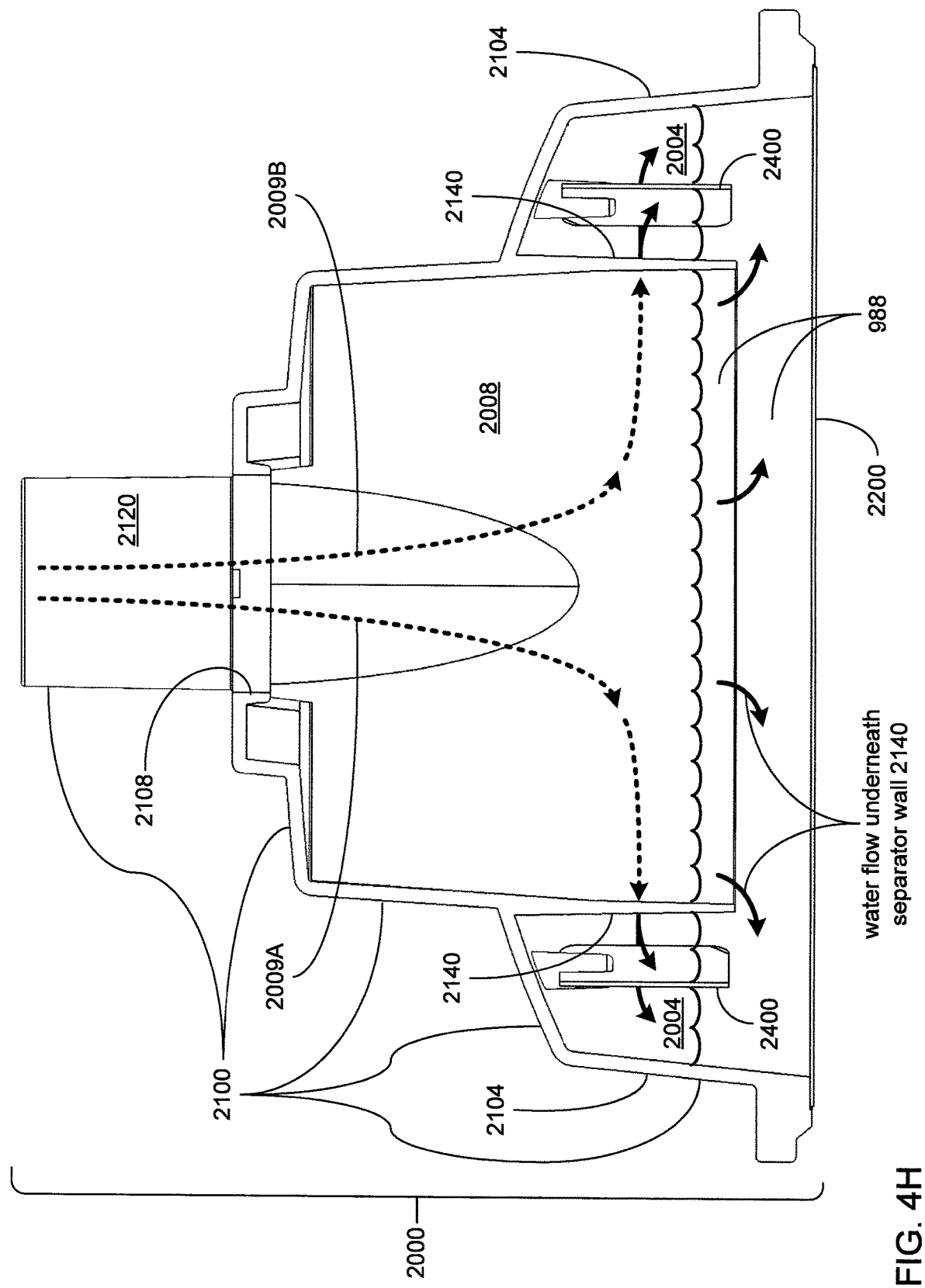
FIG. 4H is an elevational view thereof, also with a complete casing bottom and half of the casing top cut away along a sectional plane that again cuts through the casing top at a location between the gas inlet and gas outlet, and showing part of each of the paths taken by flows of respiratory gases therethrough, as well as additionally depicting a water level of the water to be maintained therein during humidification of the respiratory gases that flow therethrough.
Figure 41:
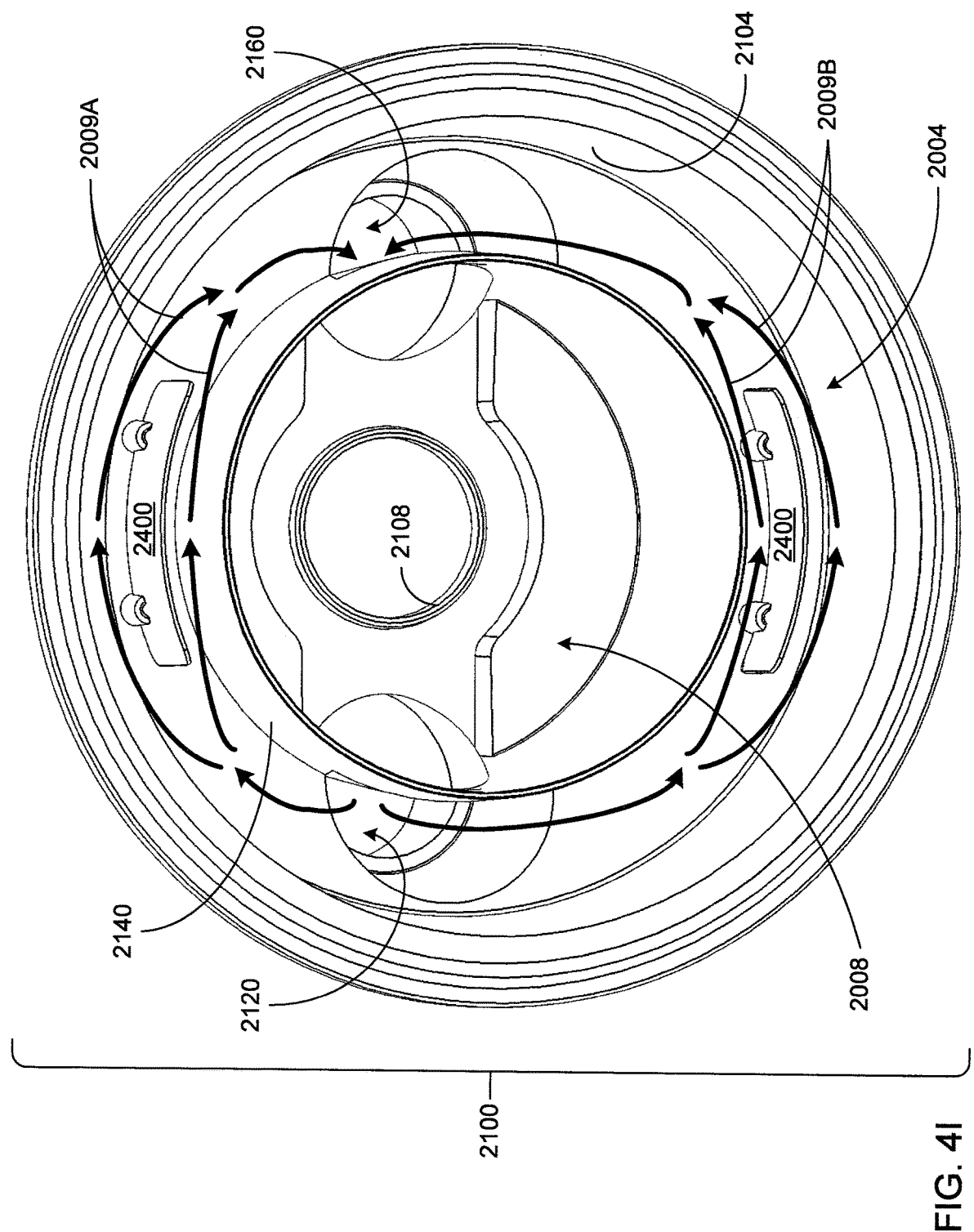

Along with FIG. 4I, each of FIGS. 4G-H also depicts the positioning of one each of the heat exchangers 2400 within each of these elongated tube-like pathways defined by the outer wall 2104, the separator wall 2140 and the surface of the water 988. As depicted, each of the heat exchangers 2400 may be suspended within its respective tube-like pathway so as to extend partially into the water 988 therein, but not deep enough to make contact with the casing bottom 2200. As previously discussed, the water within both of the chambers 2004 and 2008 is heated by a ventilator, CPAP device or other medical device through the thermally conductive casing bottom 2200 to excite the molecules of the water 988 therein. Additionally, such heating of the water 988 also serves to indirectly heat the respiratory gases that flow through the respiratory humidification device 2000 to thereby cause increase the absorption capacity of those respiratory gases.

Each of the heat exchangers 2400 may be formed from a sheet of metal or other thermally conductive material to absorb some of the heat in the water 988 within the annular humidification chamber 2004 and radiate it into the respiratory gases flowing along respective ones of the paths 2009A and 2009B. FIG. 4I most clearly depicts the further splitting of the semi-circular gas flows along each of the paths 2009A and 2009B to cause flowing of those gases along both sides of each of the heat exchangers 2400, thereby enabling each heat exchanger 2400 to radiate heat into more of the flow of respiratory gases along each path 2009A and 2009B than may be reached by heat rising (or otherwise being imparted to these gas flows) from the surface of the water 988. As additionally depicted in FIG. 4I, each of the heat exchangers 2400 may be given a curved shape to better follow respective ones of the paths 2009A and 2009B. Alternatively or additionally, in various embodiments, each of the heat exchangers 2400 may be shaped, sized and/or positioned within respective ones of the tube-like pathways followed by respective ones of the paths 2009A and 2009B to aid in inducing and/or shaping a horizontally extending vortex of the respiratory gases flowing therethrough, as previously discussed.

FIGS. 5A through 5F depict aspects of the cooperation among the valve 2800, and the two floats 2600 and 2700 (originally introduced in FIG. 4C for the more detailed embodiment of FIGS. 4A-I, but which may also be included in the simplified embodiment of FIGS. 3A-H) to control the amount of water that enters the respiratory humidification device 2000, and thereby control the level of the water 988 within the chambers 2004 and 2008. As previously discussed, as the water 988 within the annular humidification chamber 2004 is absorbed into the two semi-circular flows of respiratory gases along the paths 2009A and 2009B therethrough, the water 988 therein is replenished from the central filling chamber 2008 through the space between the bottom most edge of the separator wall 2140 and the casing bottom 2200. In turn, the water 988 within the central filling chamber 2008 is replenished through the water inlet 2180.

However, although such an inflow of water into the respiratory humidification device 2000 is necessary to its function of humidifying respiratory gases, such an inflow of water does come with risks. By way of example, if too much water enters the respiratory humidification device 2000, the water 988 may be output through the gas outlet 2160 and sent onward to a patient who may be harmed by the inhalation of liquid water. To prevent this, each of the floats 2600 and 2700 may be positioned within the central filling chamber 2008 to float on the surface of the water 988 therein, independently of each other. Also, each of the floats 2600 and 2700 may be guided therein for vertical movement by which either or both of the floats 2600 and 2700 may be caused to engage the valve 2800 to cause the valve 2800 to close the inlet 2180 in response to the level of the water 988 within the central filling chamber 2008 rising above a predetermined threshold maximum level. As will be explained in greater detail, each of the two floats 2600 and 2700 may interact with the valve 2800 in a manner that is entirely independent of the other such that the two floats 2600 and 2700 are redundant to each other such that one will still function to operate the valve 2800 if the other fails.

Figure 5A:
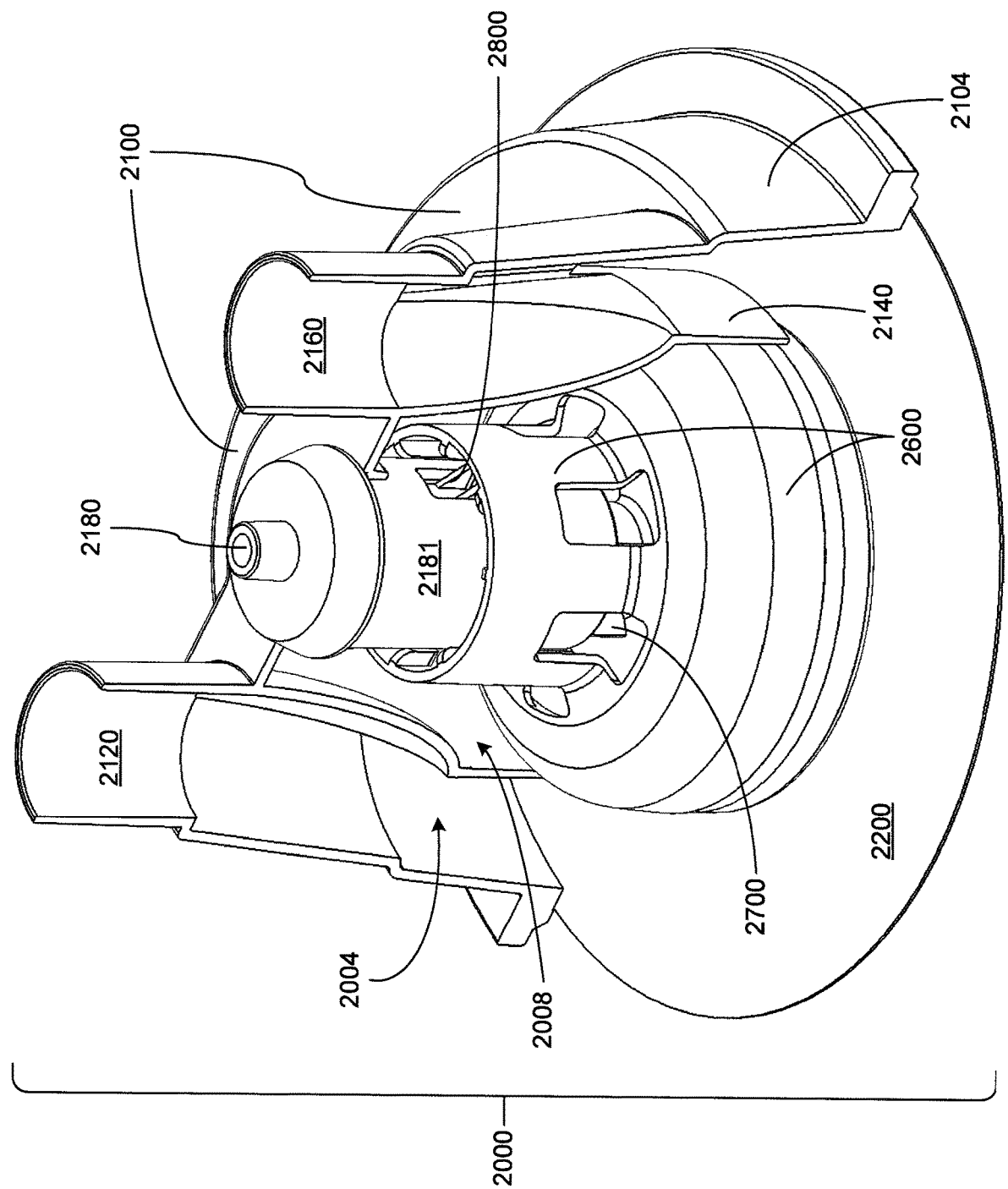
FIG. 5A is another perspective view of the example embodiment of the novel humidification device of FIGS. 4A-H with a complete casing bottom, but with half of the casing top cut away along a sectional plane that, cuts through both the gas inlet and gas outlet of the casing top, and showing the complete valve and the pair of floats assembled therein.
Figure 5B:
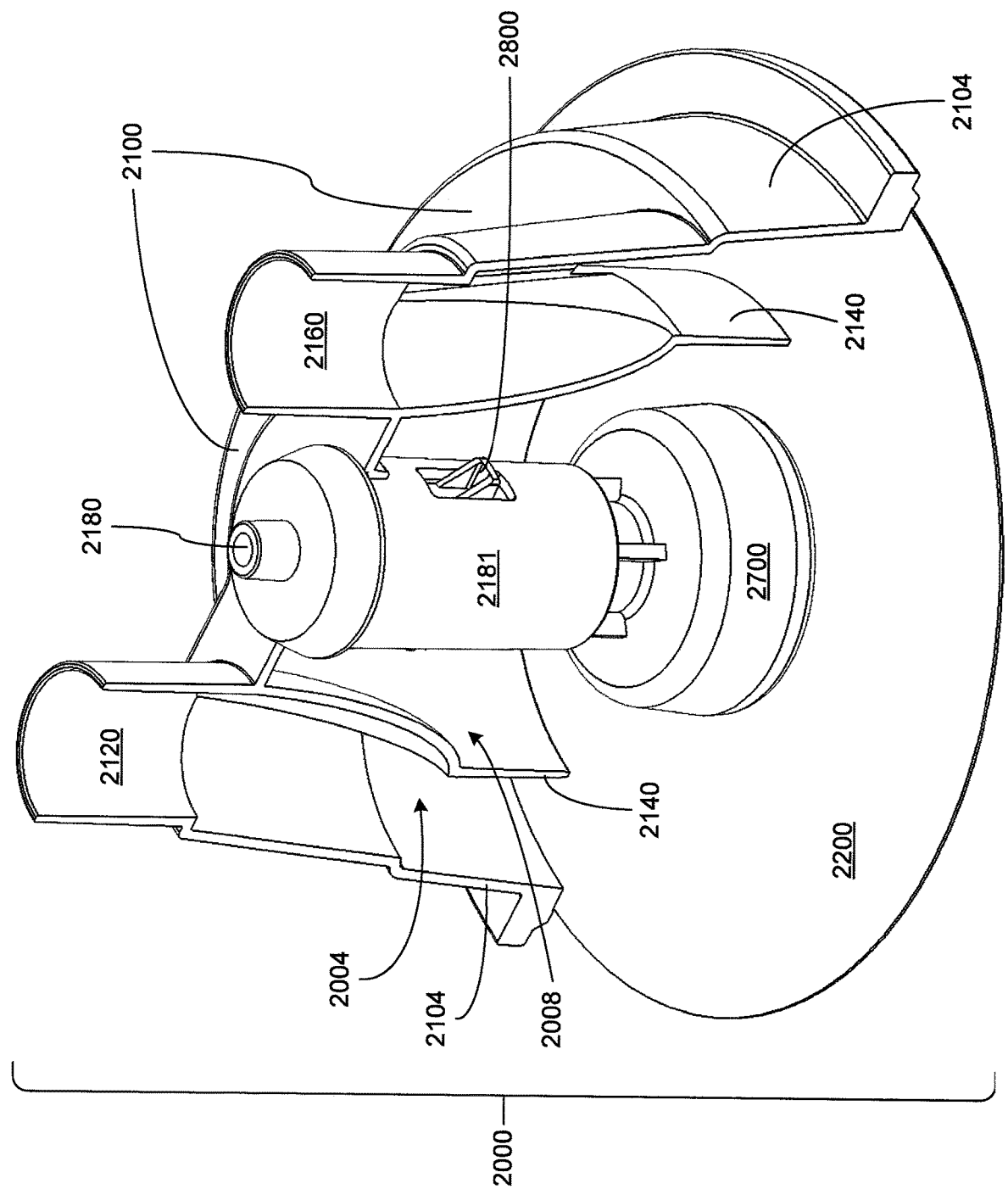
FIG. 5B is another, nearly identical, perspective view thereof showing the complete valve and a smaller one of the pair of floats, but not showing the larger one of the pair of floats.
Figure 5C:
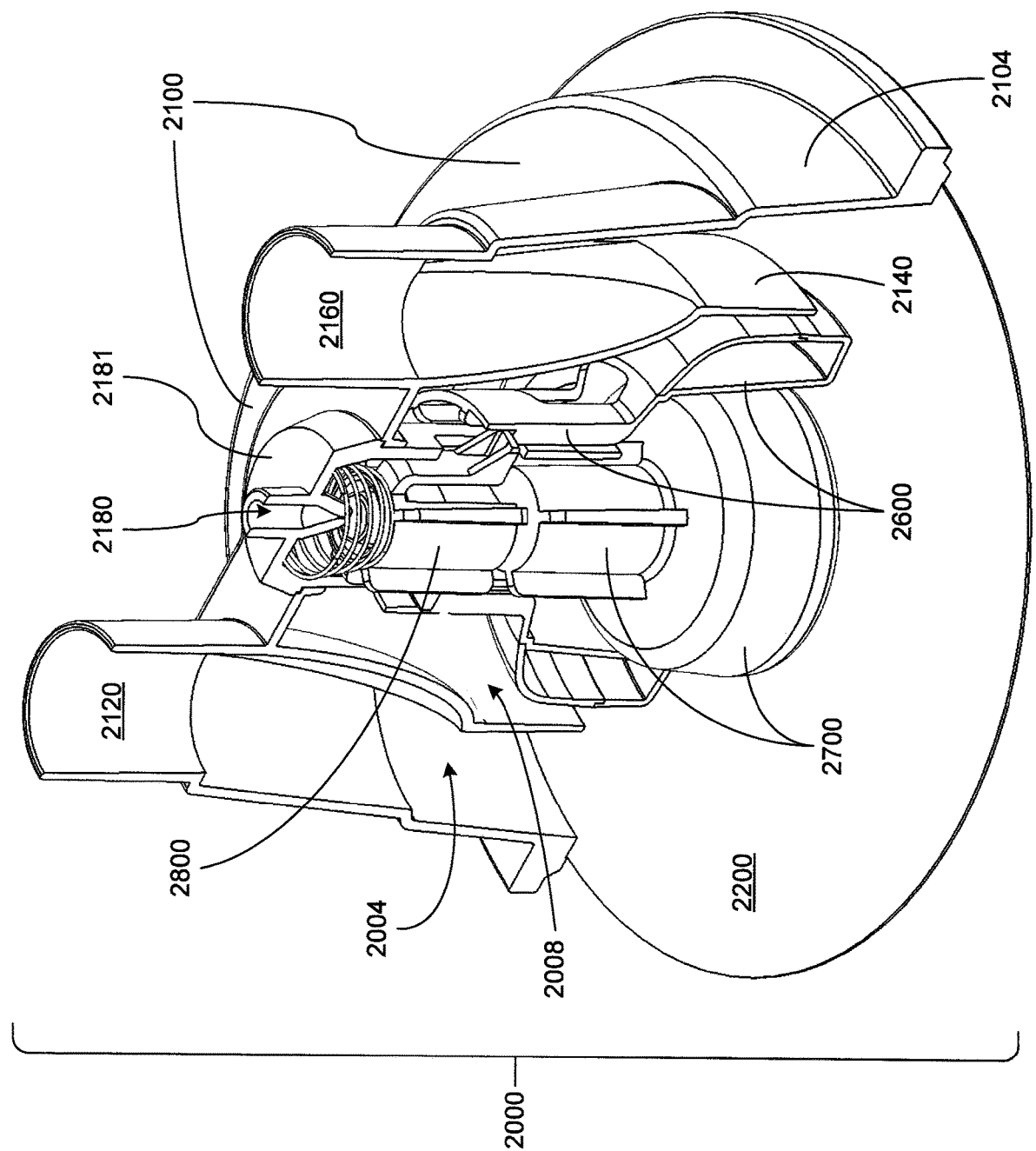
FIG. 5C is another, nearly identical, perspective view thereof showing the valve and the pair of floats, but with the valve guide of the valve and with the larger one of the pair of floats cut away along the same sectional plane.

As best seen in FIGS. 5A-C, such guidance for such vertical movement may be provided by a valve guide 2181 that forms the part of the casing top 2100 and is fabricated to be mounted within the earlier-discussed guide aperture 2108. As depicted, the valve 2800 is carried within the valve guide 2181 in a manner that supports the valve 2800 for vertical movement therein. Also extending into the valve guide 2181 from underneath the valve guide 2181 is a float top 2701 that defines an upper most surface of an upper portion of the small float 2700. As also depicted, the small float and a lower portion of the valve guide 2181 are both surrounded by the large float 2700.

Figure 5D:
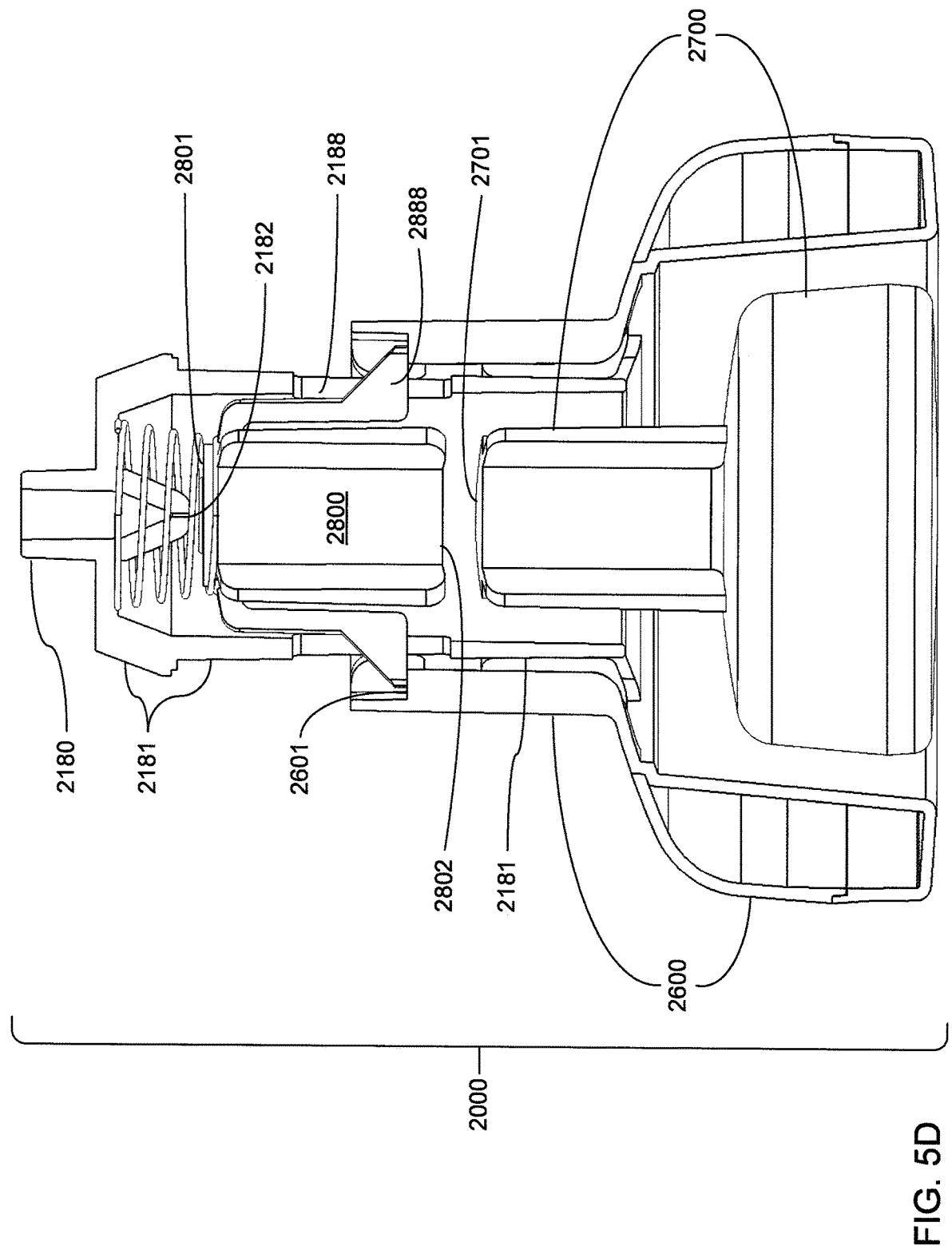
FIG. 5D is an elevational view of the valve and the pair of floats, but with half of the valve guide and the larger one of the pair of floats cut away.
Figure 5E:
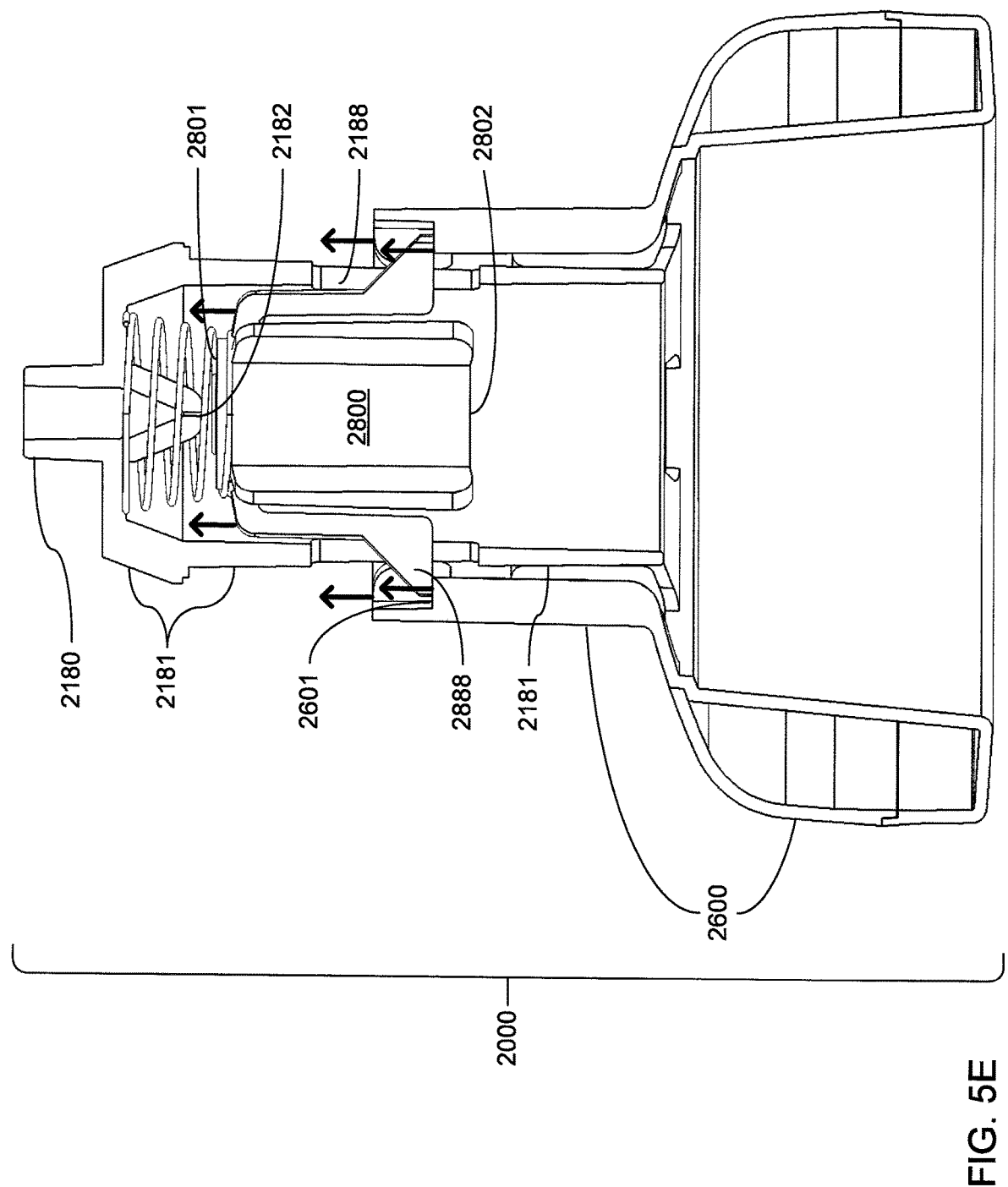
FIG. 5E is another, nearly identical, elevational view thereof showing the valve and the larger one of the pair of floats, and with half the valve guide and the larger one of the pair of floats cut away, but not showing the smaller one of the pair of floats.
Figure 5F:
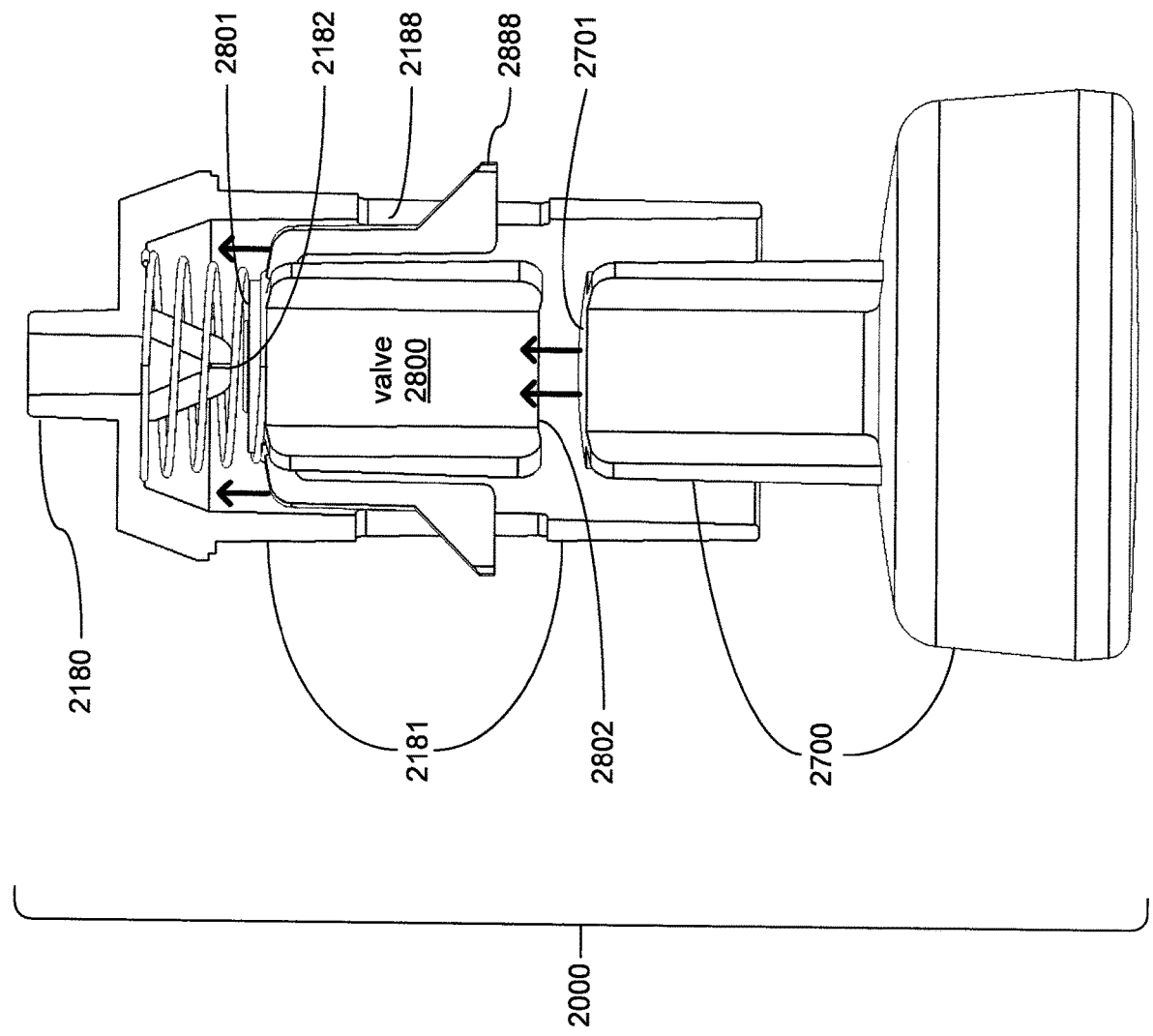
FIG. 5F is another, nearly identical, elevational view thereof showing the valve and the smaller one of the pair of floats, and with half the valve guide cut away, but not showing the larger one of the pair of floats.

As best seen in FIGS. 5D and 5F, the positioning of the upper portion of the small float 2700 within the valve guide 2181 positions the float top 2701 to engage a valve bottom 2802 that defines the lower most surface of the valve 2800 to lift the valve 2800 upward within the valve guide 2181 in response to a rising water level within the central filling chamber 2008. If the valve 2800 is so lifted sufficiently high within the valve guide 2181 from underneath by the small float 2700, then a valve top 2801 that defines the upper most surface of the valve 2800 may be pressed against an inlet tip 2182 of the water inlet 2180, thereby closing the water inlet 2180 so as to not allow more of the water 988 to enter the respiratory humidification device 2000.

Correspondingly, as best seen in FIGS. 5D-E, the positioning of the upper portion of the large float 2600 to surround the valve guide 2181 positions a pair of float tops 2601 that define upwardly facing surfaces of the large float 2700 to engage corresponding valve tabs 2888 that protrude through corresponding tab guides 2188 formed through the wall of the valve guide 2181 to lift the valve 2800 upward within the valve guide 2181 in response to a rising level of the water 988 within the central filling chamber 2008. As with lifting of the valve 2800 by the small float 2700, if the valve 2800 is lifted sufficiently high within the valve guide 2181 by engagement with the valve tabs 2888 by the float tops 2601 of the large float 2600, then the valve top 2801 may be pressed against the inlet tip 2182 of the water inlet 2180, thereby closing the water inlet 2180.

Figure 6A:
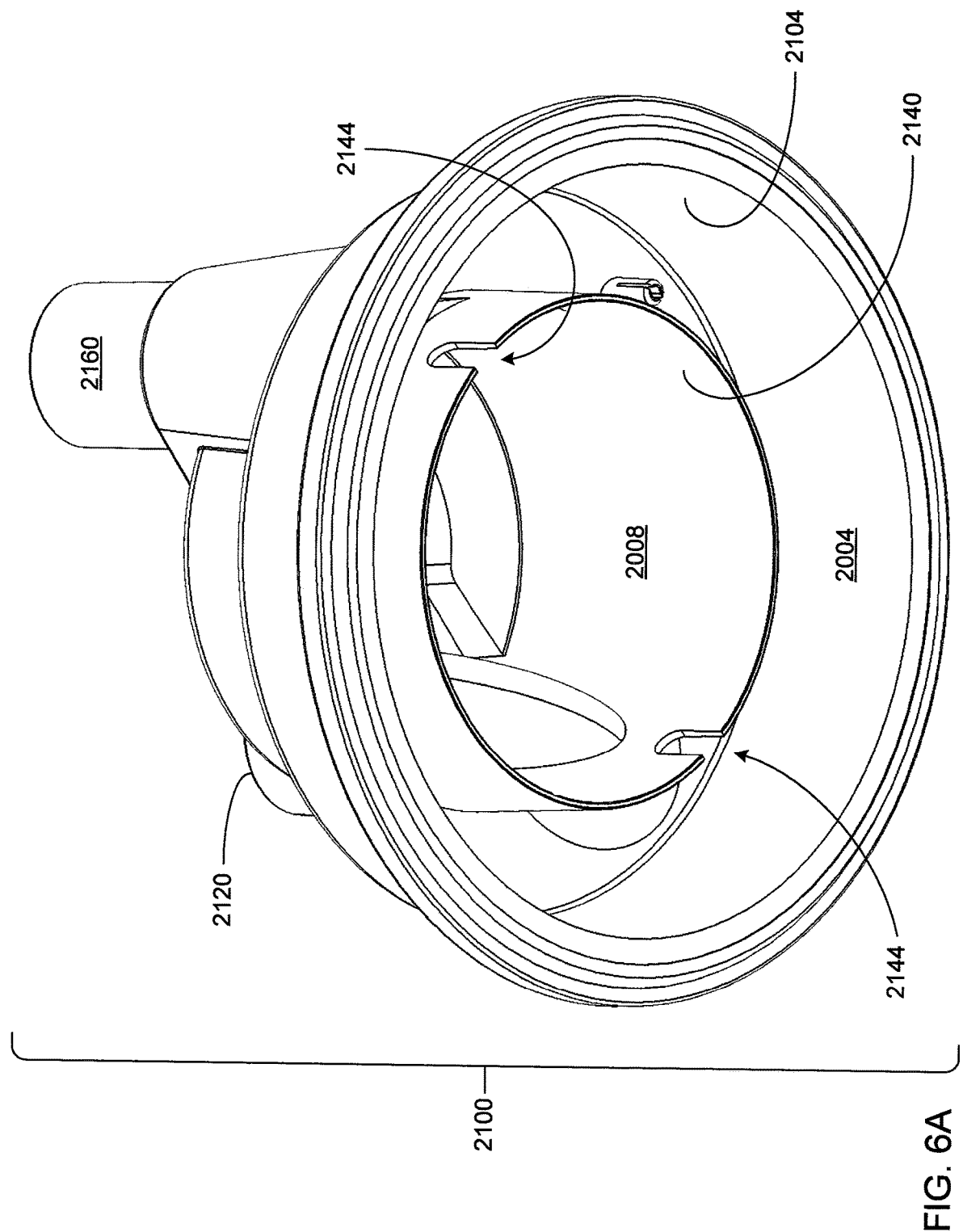
FIG. 6A is a perspective view, from underneath, of a casing top of an alternate example embodiment of the novel humidification device of FIGS. 4A-H showing a pair of separator notches formed through a separator wall thereof.
Figure 6B:
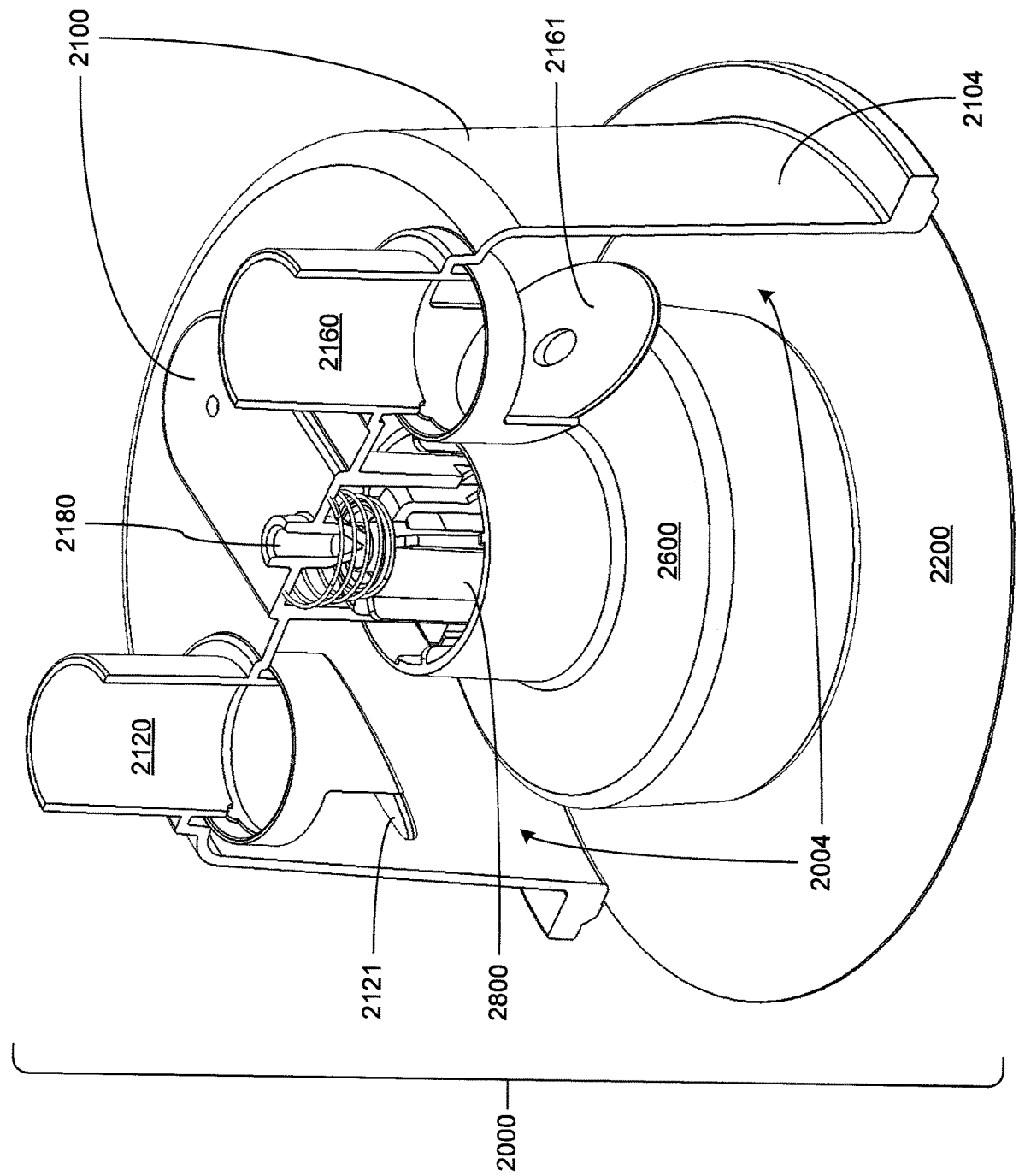
FIG. 6B is a perspective view of another alternate example embodiment of the novel humidification device of FIGS. 5A-F with an alternate embodiment of the larger one of the pair of floats serving to additionally replace the separator wall thereof, and with a pair of guides at the gas inlet and gas outlet to guide the flow of respiratory gases therethrough.

Each of FIGS. 6A and 6B depicts details of alternate embodiments of the respiratory humidification device 2000. Turning to FIG. 6A, it may be that differences in pressure between the chambers 2004 and 2008 may cause unpredictable raising or lowering of the water level within the annular humidification chamber 2004 such that water therein may be output through the gas outlet 2160 while the water level within the central filling chamber 2008 remains low enough that operation of the valve 2800 to close the water inlet 2180 is not triggered by either of the floats 2600 or 2700. As an approach to address such a possibility, in one alternate embodiment, at least one separator notch 2144 may be formed along the bottom edge of the separator wall 2140 to provide a pathway above what is intended to be the water line to allow gas to be exchanged between the two chambers 2004 and 2008. As depicted, the positioning of each such separator notch 2144 may be directly below (or nearly directly below) one of the gas inlet 2120 or the gas outlet 2160.

From various tests, it appears that such positioning of one or two of such separator notches 2144 in the vicinity of where the flow of respiratory gases is either divided into the two semi-circular gas flows that proceed along the paths 2009A and 2009B or in the vicinity of where they are recombined causes negligible disruption to the flow of respiratory gases, at least in comparison to positioning any of such separator notches along either of the paths 2009A or 2009B.

Turning to FIG. 6B, in another alternate embodiment of the respiratory humidification device 2000, the large float 2600 may be shaped and sized to at least partially serve the function of the separator wall 2140 in defining a pair of elongate tube-like semicircular pathways in lieu of having the separator wall 2140 to do so. Additionally, the direction of the flow of respiratory gases in the vicinity of where they are split into the two semi-circular gas flows and in the vicinity of where the two semi-circular gas flows recombine may be controlled by the addition of an inlet guide 2121 just beneath the gas inlet 2120 and a corresponding outlet guide 2161 just beneath gas outlet 2160.

Although the invention has been described in a preferred form with a certain degree of particularity, it is understood that the present disclosure of the preferred form has been made only by way of example, and that numerous changes in the details of construction and the manner of manufacture may be resorted to without departing from the spirit and scope of the invention. It is intended to protect whatever features of patentable novelty exist in the invention disclosed.

The invention claimed is:

1. A respiratory humidification device comprising:
   a casing comprising a casing top and a casing bottom that cooperate to enclose an interior space, wherein the casing bottom defines an underside portion of the casing that is formed from thermally conductive material to conduct heat into the interior space from a heating component positioned external to and underneath the casing to heat water within the casing;
   a separator wall within the interior space that extends downward from the casing top and toward the casing bottom to divide the interior space into a filling chamber and a humidification chamber, wherein a bottom edge of the separator wall leaves a space between the separator wall and the casing bottom that defines a main passage between the filling chamber and the humidification chamber that allows the water to flow atop the casing bottom between the filling chamber and the humidification chamber, and that enables a level of the water within at least one of the filling chamber or the humidification chamber to rise high enough to block the main passage to prevent respiratory gas from passing therethrough;
   a valve and a first float within the filling chamber that cooperate to control a flow of the water into the filling chamber from a water source external to the casing to prevent the level of the water within at least the filling chamber from rising higher than a predetermined threshold level;
   a gas inlet formed through the casing top to enable entry of a main flow of the respiratory gas into the humidification chamber from a medical device external to the casing;
   a gas outlet formed through the casing top to enable the main flow of respiratory gas to proceed through the humidification chamber in a direction from the gas inlet to the gas outlet, and to be output from the gas outlet to a patient after humidification of the respiratory gas, wherein:
      at least one portion of an outer wall of the casing top and at least one portion of the separator wall are configured to cooperate with a surface of the water within the humidification chamber to define an elongate tube-like pathway between the gas inlet and the gas outlet through which at least one portion of the main flow of the respiratory gas is to proceed along a path that extends generally parallel to the surface of the water within the humidification chamber to enable humidification of the respiratory gas with the water within the humidification chamber; and
   a heat spreader within the humidification chamber, wherein a lower portion of the heat spreader is positioned to extend downward into the water within the humidification chamber to absorb heat from the water within the humidification chamber, and an upper portion of the heat spreader is positioned to extend upward from the surface of the water within the humidification chamber and into the path of the at least one portion of the main flow of the respiratory gas to radiate the absorbed heat into the respiratory gas to enhance the humidification of the respiratory gas within the humidification chamber.

2. The respiratory humidification device of claim 1, wherein the casing bottom is shaped and sized to enable the respiratory humidification device to be supported by the casing bottom atop the heating component to place the casing bottom in thermally conductive contact with the heating component.

3. The respiratory humidification device of claim 1, wherein the casing bottom defines at least a portion of both the filling chamber and the humidification chamber to enable heating of the water within both the filling chamber and the humidification chamber through the casing bottom by the heating component.

4. The respiratory humidification device of claim 1, wherein the casing top is formed from a thermally insulating material to increase retention, within the interior space, of the heat provided to the respiratory humidification device by the heating component.

5. The respiratory humidification device of claim 1, wherein another passage is formed through the separator wall to enable another flow of the respiratory gas between the filling chamber and the humidification chamber that enables equalization of gas pressure between the filling chamber and the humidification chamber to enable the levels of the water within the filling chamber and the humidification chamber to be equalized at times when the level of the water within at least one of the filling chamber and the humidification chamber is high enough to block the main passage, wherein the other passage is smaller than the gas inlet, the gas outlet and the main passage, and wherein the other flow of the respiratory gas is smaller than the main flow of respiratory gas.

6. The respiratory humidification device of claim 1, further comprising a second float within the filling chamber to cooperate with the valve to control the flow of the water into the filling chamber from the water source to prevent the level of the water within at least the filling chamber from rising higher than the predetermined threshold level, wherein the cooperation between the valve and the first float to control the flow of the water into the filling chamber from the water source is independent of the cooperation between the valve and the second float to control the flow of the water into the filling chamber from the water source such that either of the cooperation between the valve and the first float or the cooperation between the valve and the second float is able to cause the flow of water in the filling chamber from the water source to be stopped to prevent the level of the water within at least the filling chamber from rising higher than the predetermined threshold level.

7. The respiratory humidification device of claim 6, wherein the first float is larger than and concentrically surrounds the second float.

8. The respiratory humidification device of claim 1, wherein:
at least a portion of the gas inlet and at least a portion of the gas outlet are of an identical shape and size to enable the medical device to be connected to the gas outlet to cause the main flow of respiratory gas to proceed in an opposite direction through the humidification chamber from the gas outlet to the gas inlet, and to be output from the gas inlet to the patient; and
the elongate tube-like pathway is configured to enable the humidification of the respiratory gas to be as effective when the main flow proceeds in the opposite direction from the gas outlet to the gas inlet as in the direction from the gas inlet to the gas outlet.

9. The respiratory humidification device of claim 1, wherein the at least one portion of the outer wall and the at least one portion of the separator wall are configured to cooperate with the surface of the water within the humidification chamber to induce a horizontal vortex in the at least one portion of the main flow of the respiratory gas along the path to enhance the humidification of the respiratory gas within the humidification chamber.

10. The respiratory humidification device of claim 1, wherein the heat spreader is configured to cooperate with at least one of the at least one portion of the outer wall, the at least one portion of the separator wall or the surface of the water within the humidification chamber to induce a horizontal vortex in the at least one portion of the main flow of the respiratory gas along the path to enhance the humidification of the respiratory gas within the humidification chamber.

11. The respiratory humidification device of claim 1, wherein:
at least the portion of the outer wall is formed to give at least a portion of the casing top a curve in its shape; and
at least the portion of the outer wall and at least the portion of the separator wall are configured to cooperate with the surface of the water within the humidification chamber to define the elongate tube-like pathway to be a semi-circular elongate tube-like pathway such that at least the portion of the main flow of the respiratory gas follows a semi-circular path between the gas inlet and the gas outlet.

12. The respiratory humidification device of claim 11, wherein:
the outer wall is formed to give at least a portion of the casing a cylindrical shape;
the separator wall is formed to define the humidification chamber as an annular humidification chamber that surrounds the filling chamber such that the filling chamber is nested concentrically within the annular humidification chamber;
the outer wall and the separator wall are configured to cooperate with the surface of the water within the annular humidification chamber to define a pair of semi-circular elongate tube-like pathways between the gas inlet and the gas outlet;
the at least one portion of the main flow of the respiratory gas proceeds along the path that extends generally parallel to the surface of the water within the humidification chamber and through a first one of the pair of semi-circular elongate tube-like pathways; and
at least one other portion of the main flow of the respiratory gas proceeds along another path that extends generally parallel to the surface of the water within the humidification chamber and through an second one of the pair of semi-circular elongate tube-like pathways.

13. The respiratory humidification device of claim 1, wherein:
the medical device monitors at least one of a temperature and a rate of flow of the main flow of the respiratory gas from the respiratory humidification device to the patient; and
the medical device adjusts an amount of the heat provided by the heating component to at least the casing bottom based on the at least one of the temperature and the rate of flow.

14. The respiratory humidification device of claim 1, further comprising the heating component.

15. The respiratory humidification device of claim 1, further comprising the medical device.

16. The respiratory humidification device of claim 1, further comprising an inspiratory hose assembly to convey the main flow of the respiratory gas from the humidification device after the humidification of the respiratory gas.

17. The respiratory humidification device of claim 16, further comprising an expiratory hose assembly to convey exhaled respiratory gas from the patient to the medical device.

\* \* \* \* \*